United States Patent
Saito

(10) Patent No.: US 10,966,843 B2
(45) Date of Patent: Apr. 6, 2021

(54) IMPLANT INSERTERS AND RELATED METHODS

(71) Applicant: DePuy Synthes Products, Inc., Raynham, MA (US)

(72) Inventor: Koki Saito, Tokyo (JP)

(73) Assignee: DePuy Synthes Products, Inc., Raynham, MA (US)

(*) Notice: Subject to any disclaimer, the term of this patent is extended or adjusted under 35 U.S.C. 154(b) by 48 days.

(21) Appl. No.: 16/037,168

(22) Filed: Jul. 17, 2018

(65) Prior Publication Data

US 2019/0038434 A1  Feb. 7, 2019

Related U.S. Application Data

(60) Provisional application No. 62/534,039, filed on Jul. 18, 2017.

(51) Int. Cl.
  *A61F 2/46*  (2006.01)
  *A61F 2/30*  (2006.01)

(52) U.S. Cl.
  CPC .......... *A61F 2/4611* (2013.01); *A61F 2/4603* (2013.01); *A61F 2002/30507* (2013.01); *A61F 2002/30538* (2013.01); *A61F 2002/4622* (2013.01); *A61F 2002/4627* (2013.01); *A61F 2002/4628* (2013.01)

(58) Field of Classification Search
  CPC ........ A61F 2/46; A61F 2/4603; A61F 2/4611; A61F 2002/4625; A61F 2002/4627
  See application file for complete search history.

(56) References Cited

U.S. PATENT DOCUMENTS

| | | |
|---|---|---|
| 3,426,364 A | 2/1969 | Lumb |
| 3,867,728 A | 2/1975 | Stubstad et al. |
| 4,105,034 A | 8/1978 | Shalaby et al. |
| 4,130,639 A | 12/1978 | Shalaby et al. |
| 4,140,678 A | 2/1979 | Shalaby et al. |

(Continued)

FOREIGN PATENT DOCUMENTS

| | | |
|---|---|---|
| CA | 2446934 A1 | 11/2002 |
| CA | 2534357 A1 | 2/2005 |

(Continued)

OTHER PUBLICATIONS

AcroMed Carbon Fiber Interbody Fusion Devices; Jan. 1998, 8 pages.

(Continued)

*Primary Examiner* — Lynnsy M Summitt
(74) *Attorney, Agent, or Firm* — Nutter McClennen & Fish LLP

(57) ABSTRACT

Implant inserters and related methods are disclosed herein, e.g., for delivering a fusion cage or other implant to a spinal disc space and for rotating or articulating the implant within the disc space. An exemplary instrument can include a slider that is slidably mounted to a body to define an implant clamp. A locking mechanism can allow the slider to be quickly disassembled from the body and for fast and convenient loading and unloading of an implant to the instrument. An actuation knob can be moved between a first position in which the implant is locked from rotating relative to the instrument and a second position in which the implant is retained to the instrument but allowed to rotate relative to the instrument.

11 Claims, 22 Drawing Sheets

(56) References Cited

U.S. PATENT DOCUMENTS

| | | |
|---|---|---|
| 4,141,087 A | 2/1979 | Shalaby et al. |
| 4,205,399 A | 6/1980 | Shalaby et al. |
| 4,208,511 A | 6/1980 | Shalaby et al. |
| 4,298,993 A | 11/1981 | Kovaleva et al. |
| 4,349,921 A | 9/1982 | Kuntz |
| 4,394,370 A | 7/1983 | Jefferies |
| 4,450,591 A | 5/1984 | Rappaport |
| 4,454,374 A | 6/1984 | Pollack |
| 4,538,612 A | 9/1985 | Patrick, Jr. |
| 4,545,374 A | 10/1985 | Jacobson |
| 4,599,086 A | 7/1986 | Doty |
| 4,627,853 A | 12/1986 | Campbell et al. |
| 4,714,469 A | 12/1987 | Kenna |
| 4,743,256 A | 5/1988 | Brantigan |
| 4,781,721 A | 11/1988 | Grundei |
| 4,829,152 A | 5/1989 | Rostoker et al. |
| 4,834,757 A | 5/1989 | Brantigan |
| 4,863,476 A | 9/1989 | Shepperd |
| 4,872,452 A | 10/1989 | Alexson |
| 4,877,020 A | 10/1989 | Vich et al. |
| 4,878,915 A | 11/1989 | Brantigan |
| 4,904,261 A | 2/1990 | Dove et al. |
| 4,911,718 A | 3/1990 | Lee et al. |
| 4,917,704 A | 4/1990 | Frey et al. |
| 4,927,425 A | 5/1990 | Lozier |
| 4,941,481 A | 7/1990 | Wagenknecht |
| 4,955,908 A | 9/1990 | Frey et al. |
| 4,995,200 A | 2/1991 | Eberhart |
| 4,997,432 A | 3/1991 | Keller |
| 5,006,120 A | 4/1991 | Carter |
| 5,006,121 A | 4/1991 | Hafeli |
| 5,015,247 A | 5/1991 | Michelson |
| 5,019,082 A | 5/1991 | Frey et al. |
| 5,047,058 A | 9/1991 | Roberts et al. |
| 5,116,374 A | 5/1992 | Stone |
| 5,123,926 A | 6/1992 | Pisharodi |
| 5,133,719 A | 7/1992 | Winston |
| 5,163,939 A | 11/1992 | Winston |
| 5,169,402 A | 12/1992 | Elloy |
| 5,171,240 A | 12/1992 | Hanwong |
| 5,171,278 A | 12/1992 | Pisharodi |
| 5,171,281 A | 12/1992 | Parsons et al. |
| 5,190,549 A | 3/1993 | Miller et al. |
| 5,192,327 A | 3/1993 | Brantigan |
| 5,201,736 A | 4/1993 | Strauss |
| 5,217,475 A | 6/1993 | Kuber |
| 5,250,061 A | 10/1993 | Michelson |
| 5,258,031 A | 11/1993 | Salib et al. |
| 5,282,861 A | 2/1994 | Kaplan |
| 5,298,254 A | 3/1994 | Prewett et al. |
| 5,306,307 A | 4/1994 | Senter et al. |
| 5,306,308 A | 4/1994 | Gross et al. |
| 5,306,309 A | 4/1994 | Wagner et al. |
| 5,320,644 A | 6/1994 | Baumgartner |
| 5,342,365 A | 8/1994 | Waldman |
| 5,387,215 A | 2/1995 | Fisher |
| 5,390,683 A | 2/1995 | Pisharodi |
| 5,397,364 A | 3/1995 | Kozak et al. |
| 5,425,772 A | 6/1995 | Brantigan |
| 5,431,658 A | 7/1995 | Moskovich |
| 5,443,514 A | 8/1995 | Steffee |
| 5,443,515 A | 8/1995 | Cohen et al. |
| 5,454,815 A | 10/1995 | Geisser et al. |
| 5,454,827 A | 10/1995 | Aust et al. |
| 5,464,929 A | 11/1995 | Bezwada et al. |
| 5,476,466 A | 12/1995 | Barrette et al. |
| 5,484,437 A | 1/1996 | Michelson |
| 5,522,899 A | 6/1996 | Michelson |
| 5,540,693 A | 7/1996 | Fisher |
| 5,545,229 A | 8/1996 | Parsons et al. |
| 5,550,172 A | 8/1996 | Regula et al. |
| 5,554,191 A | 9/1996 | Lahille |
| 5,556,431 A | 9/1996 | Buttner-Janz |
| 5,595,751 A | 1/1997 | Bezwada et al. |
| 5,597,579 A | 1/1997 | Bezwada et al. |
| 5,601,561 A | 2/1997 | Terry et al. |
| 5,607,687 A | 3/1997 | Bezwada et al. |
| 5,609,635 A | 3/1997 | Michelson |
| 5,618,552 A | 4/1997 | Bezwada et al. |
| 5,620,448 A | 4/1997 | Puddu |
| 5,620,698 A | 4/1997 | Bezwada et al. |
| 5,645,596 A | 7/1997 | Kim et al. |
| 5,645,850 A | 7/1997 | Bezwada et al. |
| 5,648,088 A | 7/1997 | Bezwada et al. |
| 5,658,335 A | 8/1997 | Allen |
| 5,658,336 A | 8/1997 | Pisharodi |
| 5,665,122 A | 9/1997 | Kambin |
| 5,669,909 A | 9/1997 | Zdeblick et al. |
| 5,674,296 A | 10/1997 | Bryan et al. |
| 5,683,463 A | 11/1997 | Godefroy et al. |
| 5,693,100 A | 12/1997 | Pisharodi |
| 5,698,213 A | 12/1997 | Jamiolkowski et al. |
| 5,700,583 A | 12/1997 | Jamiolkowski et al. |
| 5,702,449 A | 12/1997 | McKay |
| 5,702,463 A | 12/1997 | Pothier et al. |
| 5,707,371 A | 1/1998 | Metz-Stavenhagen et al. |
| 5,725,531 A | 3/1998 | Shapiro |
| 5,728,159 A | 3/1998 | Stroever et al. |
| 5,755,798 A | 5/1998 | Papavero et al. |
| 5,766,251 A | 6/1998 | Koshino |
| 5,766,252 A | 6/1998 | Henry et al. |
| 5,772,661 A | 6/1998 | Michelson |
| 5,782,830 A | 7/1998 | Farris |
| 5,782,919 A | 7/1998 | Zdeblick et al. |
| 5,836,948 A | 11/1998 | Zucherman et al. |
| 5,857,995 A | 1/1999 | Thomas et al. |
| 5,859,150 A | 1/1999 | Jamiolkowski et al. |
| 5,860,973 A | 1/1999 | Michelson |
| 5,865,845 A | 2/1999 | Thalgott |
| 5,865,848 A | 2/1999 | Baker |
| 5,888,222 A | 3/1999 | Coates et al. |
| 5,888,223 A | 3/1999 | Bray, Jr. |
| 5,893,890 A | 4/1999 | Pisharodi |
| 5,906,616 A | 5/1999 | Pavlov et al. |
| 5,916,228 A | 6/1999 | Ripich et al. |
| 5,925,056 A | 7/1999 | Thomas |
| 5,964,807 A | 10/1999 | Gan et al. |
| 5,968,098 A | 10/1999 | Winslow |
| 5,976,187 A | 11/1999 | Richelsoph |
| 5,980,522 A | 11/1999 | Koros et al. |
| 5,989,289 A | 11/1999 | Coates et al. |
| 6,001,099 A | 12/1999 | Huebner |
| 6,008,433 A | 12/1999 | Stone |
| 6,039,761 A | 3/2000 | Li et al. |
| 6,039,762 A | 3/2000 | McKay |
| 6,045,579 A | 4/2000 | Hochshuler et al. |
| 6,053,922 A | 4/2000 | Krause et al. |
| 6,056,763 A | 5/2000 | Parsons |
| 6,066,174 A | 5/2000 | Farris |
| 6,066,175 A | 5/2000 | Henderson et al. |
| 6,080,158 A | 6/2000 | Lin |
| 6,086,593 A | 7/2000 | Bonutti |
| 6,099,531 A | 8/2000 | Bonutti |
| 6,106,557 A | 8/2000 | Robioneck et al. |
| 6,120,508 A | 9/2000 | Grunig et al. |
| 6,126,689 A | 10/2000 | Brett |
| 6,139,558 A | 10/2000 | Wagner |
| 6,143,032 A | 11/2000 | Schafer et al. |
| 6,146,421 A | 11/2000 | Gordon et al. |
| 6,159,215 A | 12/2000 | Urbahns et al. |
| 6,174,311 B1 | 1/2001 | Branch et al. |
| 6,176,882 B1 | 1/2001 | Biedermann et al. |
| 6,206,922 B1 | 3/2001 | Zdeblick et al. |
| 6,231,610 B1 | 5/2001 | Geisler |
| 6,235,059 B1 | 5/2001 | Benezech et al. |
| 6,241,733 B1 | 6/2001 | Nicholson et al. |
| 6,245,108 B1 | 6/2001 | Biscup |
| 6,251,140 B1 | 6/2001 | Marino et al. |
| 6,258,093 B1 | 7/2001 | Edwards et al. |
| 6,296,644 B1 | 10/2001 | Saurat et al. |
| 6,309,421 B1 | 10/2001 | Pisharodi |
| D450,676 S | 11/2001 | Huttner |
| 6,319,257 B1 | 11/2001 | Carignan et al. |
| 6,332,894 B1 | 12/2001 | Stalcup et al. |

(56) References Cited

U.S. PATENT DOCUMENTS

| | | |
|---|---|---|
| 6,342,074 B1 | 1/2002 | Simpson |
| 6,364,880 B1 | 4/2002 | Michelson |
| 6,371,988 B1 | 4/2002 | Pafford et al. |
| 6,387,130 B1 | 5/2002 | Stone et al. |
| 6,398,793 B1 | 6/2002 | McGuire |
| 6,409,766 B1 | 6/2002 | Brett |
| 6,413,278 B1 | 7/2002 | Marchosky |
| 6,423,095 B1 | 7/2002 | Van Hoeck et al. |
| 6,425,920 B1 | 7/2002 | Hamada |
| 6,428,544 B1 | 8/2002 | Ralph et al. |
| 6,432,106 B1 | 8/2002 | Fraser |
| 6,436,101 B1 | 8/2002 | Hamada |
| 6,443,987 B1 | 9/2002 | Bryan |
| 6,447,518 B1 | 9/2002 | Krause et al. |
| 6,447,544 B1 | 9/2002 | Michelson |
| 6,482,233 B1 | 11/2002 | Aebi et al. |
| 6,511,509 B1 | 1/2003 | Ford et al. |
| 6,579,318 B2 | 6/2003 | Varga et al. |
| 6,582,432 B1 | 6/2003 | Michelson |
| 6,595,998 B2 | 7/2003 | Johnson et al. |
| 6,599,294 B2 | 7/2003 | Fuss et al. |
| 6,605,089 B1 | 8/2003 | Michelson |
| 6,610,066 B2 | 8/2003 | Dinger et al. |
| 6,610,089 B1 | 8/2003 | Liu et al. |
| 6,635,060 B2 | 10/2003 | Hanson et al. |
| RE38,335 E | 11/2003 | Aust et al. |
| 6,641,582 B1 | 11/2003 | Hanson et al. |
| 6,648,915 B2 | 11/2003 | Sazy |
| 6,660,004 B2 | 12/2003 | Barker et al. |
| 6,676,703 B2 | 1/2004 | Biscup |
| 6,699,288 B2 | 3/2004 | Moret et al. |
| 6,719,794 B2 | 4/2004 | Gerber et al. |
| 6,733,535 B2 | 5/2004 | Michelson |
| 6,746,484 B1 | 6/2004 | Liu et al. |
| 6,755,837 B2 | 6/2004 | Ebner |
| 6,764,491 B2 | 7/2004 | Frey |
| 6,767,366 B2 | 7/2004 | Lee et al. |
| 6,830,570 B1 | 12/2004 | Frey et al. |
| 6,835,206 B2 | 12/2004 | Jackson |
| 6,835,208 B2 | 12/2004 | Marchosky |
| 6,840,941 B2 | 1/2005 | Rogers et al. |
| 6,852,127 B2 | 2/2005 | Varga et al. |
| 6,878,167 B2 | 4/2005 | Ferree |
| 6,949,108 B2 | 9/2005 | Holmes |
| 6,966,912 B2 | 11/2005 | Michelson |
| 6,974,480 B2 | 12/2005 | Messerli et al. |
| 7,018,415 B1 | 3/2006 | McKay |
| 7,048,762 B1 | 5/2006 | Sander et al. |
| 7,048,765 B1 | 5/2006 | Grooms et al. |
| 7,060,073 B2 | 6/2006 | Frey et al. |
| 7,060,096 B1 | 6/2006 | Schopf et al. |
| 7,066,961 B2 | 6/2006 | Michelson |
| 7,070,598 B2 | 7/2006 | Lim et al. |
| 7,087,055 B2 | 8/2006 | Lim et al. |
| 7,105,024 B2 | 9/2006 | Richelsoph |
| 7,112,224 B2 | 9/2006 | Liu et al. |
| 7,115,128 B2 | 10/2006 | Michelson |
| 7,115,132 B2 | 10/2006 | Errico et al. |
| 7,125,424 B2 | 10/2006 | Banick et al. |
| 7,169,182 B2 | 1/2007 | Errico et al. |
| 7,169,183 B2 | 1/2007 | Liu et al. |
| 7,192,447 B2 | 3/2007 | Rhoda |
| 7,223,292 B2 | 5/2007 | Messerli et al. |
| 7,226,482 B2 | 6/2007 | Messerli et al. |
| 7,226,483 B2 | 6/2007 | Gerber et al. |
| 7,229,477 B2 | 6/2007 | Biscup |
| 7,235,081 B2 | 6/2007 | Errico et al. |
| 7,235,082 B2 | 6/2007 | Bartish et al. |
| 7,291,173 B2 | 11/2007 | Richelsoph et al. |
| 7,311,734 B2 | 12/2007 | Van Hoeck et al. |
| 7,320,688 B2 | 1/2008 | Foley et al. |
| 7,326,248 B2 | 2/2008 | Michelson |
| 7,331,996 B2 | 2/2008 | Sato et al. |
| 7,351,262 B2 | 4/2008 | Bindseil et al. |
| 7,361,193 B2 | 4/2008 | Frey et al. |
| 7,404,795 B2 | 7/2008 | Ralph et al. |
| 7,465,305 B2 | 12/2008 | Liu et al. |
| 7,470,273 B2 | 12/2008 | Dougherty-Shah |
| 7,473,268 B2 | 1/2009 | Zucherman et al. |
| 7,481,812 B2 | 1/2009 | Frey et al. |
| 7,491,237 B2 | 2/2009 | Randall et al. |
| 7,500,991 B2 | 3/2009 | Banish, Jr. et al. |
| 7,503,920 B2 | 3/2009 | Siegal |
| 7,572,279 B2 | 8/2009 | Jackson |
| 7,575,580 B2 | 8/2009 | Lim et al. |
| 7,578,820 B2 | 8/2009 | Moore et al. |
| 7,601,173 B2 | 10/2009 | Messerli et al. |
| 7,608,080 B2 | 10/2009 | Shipp et al. |
| 7,618,458 B2 | 11/2009 | Biedermann et al. |
| 7,625,377 B2 | 12/2009 | Veldhuizen et al. |
| 7,625,394 B2 | 12/2009 | Molz, IV et al. |
| 7,655,010 B2 | 2/2010 | Serhan et al. |
| 7,655,045 B2 | 2/2010 | Richelsoph |
| 7,666,186 B2 | 2/2010 | Harp |
| 7,666,226 B2 | 2/2010 | Schaller |
| 7,670,374 B2 | 3/2010 | Schaller |
| 7,674,265 B2 | 3/2010 | Smith et al. |
| 7,682,400 B2 | 3/2010 | Zwirkoski |
| 7,703,727 B2 | 4/2010 | Selness |
| 7,704,280 B2 | 4/2010 | Lechmann et al. |
| 7,731,751 B2 | 6/2010 | Butler et al. |
| 7,763,028 B2 | 7/2010 | Lim |
| 7,771,473 B2 | 8/2010 | Thramann |
| 7,785,368 B2 | 8/2010 | Schaller |
| 7,799,081 B2 | 9/2010 | McKinley |
| 7,803,161 B2 | 9/2010 | Foley et al. |
| 7,806,932 B2 | 10/2010 | Webb et al. |
| 7,811,292 B2 | 10/2010 | Lo et al. |
| 7,828,849 B2 | 11/2010 | Lim |
| 7,832,409 B2 | 11/2010 | Richelsoph et al. |
| 7,837,734 B2 | 11/2010 | Zucherman et al. |
| 7,850,733 B2 | 12/2010 | Baynham et al. |
| 7,875,080 B2 | 1/2011 | Puno et al. |
| 7,901,458 B2 | 3/2011 | DeRidder et al. |
| 7,918,874 B2 | 4/2011 | Siegal |
| 7,922,719 B2 | 4/2011 | Ralph et al. |
| 7,935,124 B2 | 5/2011 | Frey et al. |
| 7,935,148 B2 | 5/2011 | Edie et al. |
| 7,938,857 B2 | 5/2011 | Garcia-Bengochea et al. |
| 7,942,903 B2 | 5/2011 | Moskowitz et al. |
| 7,959,675 B2 | 6/2011 | Gately |
| 7,963,967 B1 | 6/2011 | Woods |
| 7,967,863 B2 | 6/2011 | Frey et al. |
| 7,976,566 B2 | 7/2011 | Michelson |
| 7,981,156 B2 | 7/2011 | Pafford et al. |
| 7,988,695 B2 | 8/2011 | Dye |
| 7,988,699 B2 | 8/2011 | Martz et al. |
| 7,993,347 B1 | 8/2011 | Michelson |
| 7,998,209 B2 | 8/2011 | Branch et al. |
| 7,998,215 B2 | 8/2011 | Frey et al. |
| 8,007,535 B2 | 8/2011 | Hudgins et al. |
| 8,012,212 B2 | 9/2011 | Link et al. |
| 8,021,430 B2 | 9/2011 | Michelson |
| 8,025,697 B2 | 9/2011 | McClellan, III et al. |
| 8,034,110 B2 | 10/2011 | Garner et al. |
| 8,038,703 B2 | 10/2011 | Dobak, III et al. |
| 8,043,293 B2 | 10/2011 | Warnick |
| 8,048,159 B2 | 11/2011 | Ralph et al. |
| 8,057,544 B2 | 11/2011 | Schaller |
| 8,066,705 B2 | 11/2011 | Michelson |
| 8,075,622 B2 | 12/2011 | Van Hoeck et al. |
| 8,092,539 B2 | 1/2012 | Ralph et al. |
| 8,092,568 B2 | 1/2012 | Konomi et al. |
| 8,105,382 B2 | 1/2012 | Olmos et al. |
| 8,128,700 B2 | 3/2012 | Delurio et al. |
| 8,206,423 B2 | 6/2012 | Siegal |
| 8,216,317 B2 | 7/2012 | Thibodeau |
| 8,231,675 B2 | 7/2012 | Rhoda |
| 8,241,364 B2 | 8/2012 | Hansell et al. |
| 8,262,666 B2 | 9/2012 | Baynham et al. |
| 8,267,939 B2 | 9/2012 | Cipoletti et al. |
| 8,292,959 B2 | 10/2012 | Webb et al. |
| 8,343,193 B2 | 1/2013 | Johnson et al. |
| 8,343,219 B2 | 1/2013 | Allain et al. |

(56) References Cited

U.S. PATENT DOCUMENTS

| | | |
|---|---|---|
| 8,343,222 B2 | 1/2013 | Cope |
| 8,366,777 B2 | 2/2013 | Matthis et al. |
| 8,372,084 B2 | 2/2013 | Pernsteiner et al. |
| 8,382,842 B2 | 2/2013 | Greenhalgh et al. |
| 8,403,990 B2 | 3/2013 | Dryer et al. |
| 8,409,292 B2 | 4/2013 | Michelson |
| 8,435,300 B2 | 5/2013 | Messerli et al. |
| 8,444,696 B2 | 5/2013 | Michelson |
| 8,454,617 B2 | 6/2013 | Schaller et al. |
| 8,480,745 B2 | 7/2013 | Liu et al. |
| 8,491,654 B2 | 7/2013 | Frey et al. |
| 8,506,629 B2 | 8/2013 | Weiland |
| 8,579,981 B2 | 11/2013 | Lim et al. |
| 8,597,356 B2 | 12/2013 | Rhoda |
| 8,628,577 B1 | 1/2014 | Jimenez |
| 8,663,331 B2 | 3/2014 | McClellan, III et al. |
| 8,690,949 B2 | 4/2014 | Messerli et al. |
| 8,734,447 B1 | 5/2014 | Michaelson |
| 8,758,344 B2 | 6/2014 | Michelson |
| 8,758,358 B2 | 6/2014 | Errico et al. |
| 8,845,733 B2 | 9/2014 | O'Neil et al. |
| 8,845,734 B2 | 9/2014 | Weiman |
| 8,858,564 B2 | 10/2014 | Errico et al. |
| 8,858,638 B2 | 10/2014 | Michelson |
| 8,920,506 B2 | 12/2014 | McGuckin, Jr. |
| 8,926,704 B2 | 1/2015 | Glerum et al. |
| 8,940,050 B2 | 1/2015 | Laurence et al. |
| 8,956,414 B2 * | 2/2015 | Asaad .......... A61F 2/30767 606/99 |
| 8,961,609 B2 | 2/2015 | Schaller |
| 8,968,408 B2 | 3/2015 | Schaller et al. |
| 8,986,389 B2 | 3/2015 | Lim et al. |
| 9,023,109 B2 | 5/2015 | Weiland |
| 9,028,553 B2 | 5/2015 | Lindenmann et al. |
| 9,101,488 B2 | 8/2015 | Malandain |
| 9,101,492 B2 | 8/2015 | Mangione et al. |
| 9,220,607 B2 * | 12/2015 | Palmatier .......... A61F 2/4465 |
| 9,332,750 B2 | 5/2016 | Mills et al. |
| 9,358,133 B2 | 6/2016 | Lindenmann et al. |
| 9,622,879 B2 * | 4/2017 | Taylor .......... A61F 2/4611 |
| 10,070,971 B2 * | 9/2018 | Palmatier .......... A61F 2/4611 |
| 2002/0065560 A1 | 5/2002 | Varga et al. |
| 2002/0138078 A1 | 9/2002 | Chappuis |
| 2002/0138146 A1 | 9/2002 | Jackson |
| 2002/0143399 A1 | 10/2002 | Sutcliffe |
| 2002/0165550 A1 | 11/2002 | Frey |
| 2002/0165612 A1 | 11/2002 | Gerber et al. |
| 2002/0183758 A1 | 12/2002 | Middleton et al. |
| 2002/0193880 A1 | 12/2002 | Fraser |
| 2003/0023306 A1 | 1/2003 | Liu et al. |
| 2003/0028251 A1 | 2/2003 | Mathews |
| 2003/0060886 A1 | 3/2003 | Van Hoeck et al. |
| 2003/0065395 A1 | 4/2003 | Ralph et al. |
| 2003/0083747 A1 | 5/2003 | Winterbottom et al. |
| 2003/0093153 A1 | 5/2003 | Banick et al. |
| 2003/0135275 A1 | 7/2003 | Garcia et al. |
| 2003/0139812 A1 | 7/2003 | Garcia et al. |
| 2003/0139813 A1 | 7/2003 | Messerli et al. |
| 2003/0191531 A1 | 10/2003 | Berry et al. |
| 2003/0199881 A1 | 10/2003 | Bonutti |
| 2004/0002761 A1 | 1/2004 | Rogers et al. |
| 2004/0019356 A1 | 1/2004 | Fraser et al. |
| 2004/0030387 A1 | 2/2004 | Landry et al. |
| 2004/0034426 A1 | 2/2004 | Errico et al. |
| 2004/0038431 A1 | 2/2004 | Sluka et al. |
| 2004/0059337 A1 | 3/2004 | Hanson et al. |
| 2004/0059420 A1 | 3/2004 | Michelson |
| 2004/0068269 A1 | 4/2004 | Bonati et al. |
| 2004/0083000 A1 | 4/2004 | Keller et al. |
| 2004/0087947 A1 | 5/2004 | Lim et al. |
| 2004/0102784 A1 | 5/2004 | Pasquet et al. |
| 2004/0102846 A1 | 5/2004 | Keller et al. |
| 2004/0106996 A1 | 6/2004 | Liu et al. |
| 2004/0127990 A1 | 7/2004 | Bartish, Jr. et al. |
| 2004/0147129 A1 | 7/2004 | Rolfson |
| 2004/0153065 A1 | 8/2004 | Lim |
| 2004/0186574 A1 | 9/2004 | Varga et al. |
| 2004/0204714 A1 | 10/2004 | Liu et al. |
| 2004/0210308 A1 | 10/2004 | Carter et al. |
| 2004/0220668 A1 | 11/2004 | Eisermann et al. |
| 2004/0230306 A1 | 11/2004 | Hoeck et al. |
| 2005/0027360 A1 | 2/2005 | Webb et al. |
| 2005/0038431 A1 | 2/2005 | Bartish et al. |
| 2005/0096745 A1 * | 5/2005 | Andre .......... A61F 2/4465 623/17.11 |
| 2005/0107878 A1 | 5/2005 | Conchy |
| 2005/0119752 A1 | 6/2005 | Williams et al. |
| 2005/0149034 A1 | 7/2005 | Assell et al. |
| 2005/0165420 A1 | 7/2005 | Cha |
| 2005/0165484 A1 | 7/2005 | Ferree |
| 2005/0171541 A1 | 8/2005 | Boehm et al. |
| 2005/0177173 A1 | 8/2005 | Aebi et al. |
| 2005/0192241 A1 | 9/2005 | Banchereau et al. |
| 2005/0240193 A1 | 10/2005 | Layne et al. |
| 2006/0036244 A1 | 2/2006 | Spitler et al. |
| 2006/0058807 A1 | 3/2006 | Landry et al. |
| 2006/0064101 A1 | 3/2006 | Arramon |
| 2006/0064102 A1 | 3/2006 | Ebner |
| 2006/0069436 A1 | 3/2006 | Sutton et al. |
| 2006/0074429 A1 | 4/2006 | Ralph et al. |
| 2006/0100622 A1 | 5/2006 | Jackson |
| 2006/0100705 A1 | 5/2006 | Puno et al. |
| 2006/0106460 A1 | 5/2006 | Messerli et al. |
| 2006/0111715 A1 | 5/2006 | Jackson |
| 2006/0111728 A1 | 5/2006 | Abdou |
| 2006/0116767 A1 | 6/2006 | Magerl et al. |
| 2006/0122701 A1 | 6/2006 | Kiester |
| 2006/0129244 A1 | 6/2006 | Ensign |
| 2006/0142858 A1 | 6/2006 | Colleran et al. |
| 2006/0167547 A1 | 7/2006 | Suddaby |
| 2006/0189999 A1 | 8/2006 | Zwirkoski |
| 2006/0212118 A1 | 9/2006 | Abernathie |
| 2006/0229627 A1 | 10/2006 | Hunt et al. |
| 2006/0229724 A1 | 10/2006 | Lechmann et al. |
| 2006/0235426 A1 | 10/2006 | Lim et al. |
| 2006/0253120 A1 | 11/2006 | Anderson et al. |
| 2006/0254784 A1 | 11/2006 | Hartmann et al. |
| 2006/0265077 A1 | 11/2006 | Zwirkoski |
| 2006/0293753 A1 | 12/2006 | Thramann |
| 2007/0010885 A1 | 1/2007 | Liu et al. |
| 2007/0010886 A1 | 1/2007 | Banick et al. |
| 2007/0055264 A1 | 3/2007 | Parmigiani |
| 2007/0055272 A1 | 3/2007 | Schaller |
| 2007/0067035 A1 | 3/2007 | Falahee |
| 2007/0093897 A1 | 4/2007 | Gerbec et al. |
| 2007/0093901 A1 | 4/2007 | Grotz et al. |
| 2007/0118220 A1 | 5/2007 | Liu et al. |
| 2007/0142843 A1 | 6/2007 | Dye |
| 2007/0162132 A1 | 7/2007 | Messerli |
| 2007/0162138 A1 | 7/2007 | Heinz |
| 2007/0208343 A1 | 9/2007 | Magerl et al. |
| 2007/0213737 A1 | 9/2007 | Schermerhorn et al. |
| 2007/0213826 A1 | 9/2007 | Smith et al. |
| 2007/0225726 A1 * | 9/2007 | Dye .......... A61F 2/4465 606/99 |
| 2007/0225808 A1 | 9/2007 | Warnick |
| 2007/0225815 A1 | 9/2007 | Keith et al. |
| 2007/0233130 A1 | 10/2007 | Suddaby |
| 2007/0250167 A1 | 10/2007 | Bray et al. |
| 2007/0260314 A1 | 11/2007 | Biyani |
| 2007/0270957 A1 | 11/2007 | Heinz |
| 2007/0270968 A1 | 11/2007 | Baynham et al. |
| 2007/0282441 A1 | 12/2007 | Stream et al. |
| 2008/0009880 A1 | 1/2008 | Warnick et al. |
| 2008/0015701 A1 | 1/2008 | Garcia et al. |
| 2008/0027544 A1 | 1/2008 | Melkent |
| 2008/0027550 A1 | 1/2008 | Link et al. |
| 2008/0045966 A1 | 2/2008 | Buttermann et al. |
| 2008/0051890 A1 | 2/2008 | Waugh et al. |
| 2008/0058933 A1 | 3/2008 | Garner et al. |
| 2008/0065082 A1 | 3/2008 | Chang et al. |
| 2008/0077150 A1 | 3/2008 | Nguyen |
| 2008/0077153 A1 | 3/2008 | Pernsteiner et al. |
| 2008/0077241 A1 | 3/2008 | Nguyen |

(56) References Cited

U.S. PATENT DOCUMENTS

| | | |
|---|---|---|
| 2008/0077247 A1 | 3/2008 | Murillo et al. |
| 2008/0082173 A1 | 4/2008 | Delurio et al. |
| 2008/0091211 A1 | 4/2008 | Gately |
| 2008/0097454 A1 | 4/2008 | DeRidder et al. |
| 2008/0108990 A1 | 5/2008 | Mitchell et al. |
| 2008/0109083 A1 | 5/2008 | Van Hoeck et al. |
| 2008/0119935 A1 | 5/2008 | Alvarez |
| 2008/0125865 A1 | 5/2008 | Abdelgany |
| 2008/0133012 A1 | 6/2008 | McGuckin |
| 2008/0140085 A1 | 6/2008 | Gately et al. |
| 2008/0154379 A1 | 6/2008 | Steiner et al. |
| 2008/0172128 A1 | 7/2008 | Perez-Cruet et al. |
| 2008/0208255 A1 | 8/2008 | Siegal |
| 2008/0221586 A1 | 9/2008 | Garcia-Bengochea et al. |
| 2008/0221687 A1 | 9/2008 | Viker |
| 2008/0234732 A1 | 9/2008 | Landry et al. |
| 2008/0234733 A1 | 9/2008 | Scrantz et al. |
| 2008/0243126 A1 | 10/2008 | Gutierrez et al. |
| 2008/0243255 A1 | 10/2008 | Butler et al. |
| 2008/0249628 A1 | 10/2008 | Altarac et al. |
| 2008/0255563 A1 | 10/2008 | Farr et al. |
| 2008/0255574 A1 | 10/2008 | Dye |
| 2008/0269904 A1 | 10/2008 | Voorhies |
| 2008/0306488 A1 | 12/2008 | Altarac et al. |
| 2008/0312743 A1 | 12/2008 | Vila et al. |
| 2009/0030423 A1 | 1/2009 | Puno |
| 2009/0054898 A1 | 2/2009 | Gleason |
| 2009/0054911 A1 | 2/2009 | Mueller et al. |
| 2009/0062807 A1 | 3/2009 | Song |
| 2009/0076607 A1 | 3/2009 | Aalsma et al. |
| 2009/0088789 A1 | 4/2009 | O'Neil et al. |
| 2009/0105832 A1 | 4/2009 | Allain et al. |
| 2009/0112217 A1 | 4/2009 | Hester |
| 2009/0143859 A1 | 6/2009 | McClellan, III et al. |
| 2009/0164015 A1 | 6/2009 | Liu et al. |
| 2009/0182431 A1 | 7/2009 | Butler et al. |
| 2009/0192616 A1 | 7/2009 | Zielinski |
| 2009/0216234 A1 | 8/2009 | Farr et al. |
| 2009/0234364 A1 | 9/2009 | Crook |
| 2009/0240335 A1 | 9/2009 | Arcenio et al. |
| 2009/0276049 A1 | 11/2009 | Weiland |
| 2009/0299479 A1 | 12/2009 | Jones et al. |
| 2009/0317278 A1 | 12/2009 | Kokubo |
| 2010/0016968 A1 | 1/2010 | Moore |
| 2010/0030217 A1 | 2/2010 | Mitusina |
| 2010/0076502 A1 | 3/2010 | Guyer et al. |
| 2010/0094422 A1 | 4/2010 | Hansell et al. |
| 2010/0100098 A1 | 4/2010 | Norton et al. |
| 2010/0125334 A1 | 5/2010 | Krueger |
| 2010/0161060 A1 | 6/2010 | Schaller et al. |
| 2010/0174321 A1 | 7/2010 | Schaller |
| 2010/0185290 A1 | 7/2010 | Compton et al. |
| 2010/0191241 A1 | 7/2010 | McCormack et al. |
| 2010/0191337 A1 | 7/2010 | Zamani et al. |
| 2010/0198263 A1 | 8/2010 | Siegal et al. |
| 2010/0211076 A1 | 8/2010 | Germain et al. |
| 2010/0211107 A1 | 8/2010 | Muhanna |
| 2010/0217269 A1 | 8/2010 | Landes |
| 2010/0217394 A1 | 8/2010 | Michelson |
| 2010/0234849 A1 | 9/2010 | Bouadi |
| 2010/0249935 A1 | 9/2010 | Slivka et al. |
| 2010/0256768 A1 | 10/2010 | Lim et al. |
| 2010/0274358 A1 | 10/2010 | Mueller et al. |
| 2010/0280619 A1 | 11/2010 | Yuan et al. |
| 2010/0305700 A1 | 12/2010 | Ben-Arye et al. |
| 2010/0305704 A1 | 12/2010 | Messerli et al. |
| 2010/0331845 A1 | 12/2010 | Foley et al. |
| 2011/0004216 A1 | 1/2011 | Amendola et al. |
| 2011/0004314 A1* | 1/2011 | Baynham ............ A61F 2/4465 623/17.17 |
| 2011/0009970 A1 | 1/2011 | Puno |
| 2011/0029083 A1 | 2/2011 | Hynes et al. |
| 2011/0029085 A1 | 2/2011 | Hynes et al. |
| 2011/0035011 A1 | 2/2011 | Cain |
| 2011/0054529 A1 | 3/2011 | Michelson |
| 2011/0054621 A1 | 3/2011 | Lim |
| 2011/0093078 A1 | 4/2011 | Puno et al. |
| 2011/0106259 A1 | 5/2011 | Lindenmann et al. |
| 2011/0106260 A1 | 5/2011 | Laurence et al. |
| 2011/0112586 A1 | 5/2011 | Guyer et al. |
| 2011/0125266 A1 | 5/2011 | Rodgers et al. |
| 2011/0190891 A1 | 8/2011 | Suh et al. |
| 2011/0196501 A1 | 8/2011 | Michelson |
| 2011/0264218 A1* | 10/2011 | Asaad ............ A61F 2/4465 623/17.16 |
| 2011/0276142 A1 | 11/2011 | Niemiec et al. |
| 2011/0282459 A1 | 11/2011 | McClellan et al. |
| 2011/0301712 A1 | 12/2011 | Palmatier et al. |
| 2011/0319898 A1 | 12/2011 | O'Neil et al. |
| 2011/0319899 A1 | 12/2011 | O'Neil et al. |
| 2011/0319998 A1 | 12/2011 | O'Neil et al. |
| 2011/0319999 A1 | 12/2011 | O'Neil et al. |
| 2011/0320000 A1 | 12/2011 | O'Neil et al. |
| 2012/0023937 A1 | 2/2012 | Styles et al. |
| 2012/0035730 A1 | 2/2012 | Spann |
| 2012/0165943 A1 | 6/2012 | Mangione et al. |
| 2012/0209383 A1 | 8/2012 | Tsuang et al. |
| 2012/0277877 A1 | 11/2012 | Smith et al. |
| 2012/0310352 A1 | 12/2012 | DiMauro et al. |
| 2013/0006362 A1 | 1/2013 | Biedermann et al. |
| 2013/0023937 A1 | 1/2013 | Biedermann et al. |
| 2013/0035762 A1 | 2/2013 | Siegal et al. |
| 2013/0079790 A1 | 3/2013 | Stein et al. |
| 2013/0103102 A1* | 4/2013 | Taylor ............ A61F 2/4611 606/86 A |
| 2013/0109925 A1 | 5/2013 | Horton et al. |
| 2013/0110239 A1 | 5/2013 | Siegal et al. |
| 2013/0110241 A1* | 5/2013 | Palmatier ............ A61F 2/4465 623/17.16 |
| 2013/0116791 A1 | 5/2013 | Theofilos |
| 2013/0138214 A1 | 5/2013 | Greenhalgh et al. |
| 2013/0150906 A1 | 6/2013 | Kerboul et al. |
| 2013/0173004 A1 | 7/2013 | Greenhalgh et al. |
| 2013/0190875 A1 | 7/2013 | Shulock et al. |
| 2013/0238006 A1 | 9/2013 | O'Neil et al. |
| 2013/0253652 A1 | 9/2013 | Michelson |
| 2013/0268077 A1 | 10/2013 | You et al. |
| 2013/0310937 A1 | 11/2013 | Pimenta |
| 2014/0025170 A1 | 1/2014 | Lim et al. |
| 2014/0039626 A1 | 2/2014 | Mitchell |
| 2014/0039627 A1 | 2/2014 | Weiland |
| 2014/0052259 A1 | 2/2014 | Garner et al. |
| 2014/0058512 A1 | 2/2014 | Petersheim |
| 2014/0058513 A1 | 2/2014 | Gahman et al. |
| 2014/0114413 A1 | 4/2014 | Allain et al. |
| 2014/0142704 A1 | 5/2014 | Ralph et al. |
| 2014/0172103 A1 | 6/2014 | O'Neil et al. |
| 2014/0172105 A1 | 6/2014 | Frasier et al. |
| 2014/0193798 A1 | 7/2014 | Mills et al. |
| 2015/0032212 A1 | 1/2015 | O'Neil et al. |
| 2015/0094812 A1 | 4/2015 | Cain |
| 2015/0150691 A1 | 6/2015 | Lim et al. |
| 2015/0196400 A1 | 7/2015 | Dace |
| 2015/0257898 A1 | 9/2015 | Weiland |
| 2016/0038306 A1 | 2/2016 | O'Neil et al. |
| 2016/0278937 A1 | 9/2016 | Weiland |
| 2018/0303624 A1* | 10/2018 | Shoshtaev ............ A61F 2/4465 |
| 2019/0046334 A1 | 2/2019 | Dittmann et al. |

FOREIGN PATENT DOCUMENTS

| | | |
|---|---|---|
| DE | 19710392 C1 | 7/1999 |
| DE | 10241948 A1 | 4/2004 |
| DE | 10357960 B4 | 9/2015 |
| EP | 346129 A1 | 12/1989 |
| EP | 557686 A1 | 9/1993 |
| EP | 356112 B1 | 12/1993 |
| EP | 609084 A2 | 8/1994 |
| EP | 637439 A1 | 2/1995 |
| EP | 425542 B1 | 3/1995 |
| EP | 734702 A1 | 10/1996 |
| EP | 419564 B1 | 8/1998 |
| EP | 855886 A1 | 8/1998 |
| EP | 641547 B1 | 5/1999 |

(56) References Cited

FOREIGN PATENT DOCUMENTS

| | | |
|---|---|---|
| EP | 1092395 A2 | 4/2001 |
| EP | 1093760 A2 | 4/2001 |
| EP | 720455 B1 | 1/2002 |
| EP | 712607 B1 | 2/2002 |
| EP | 615428 B1 | 3/2002 |
| EP | 752830 B1 | 6/2002 |
| EP | 1222898 A3 | 8/2002 |
| EP | 1265562 A2 | 12/2002 |
| EP | 916323 B1 | 1/2003 |
| EP | 1283026 A2 | 2/2003 |
| EP | 1290985 A2 | 3/2003 |
| EP | 1294321 A1 | 3/2003 |
| EP | 836455 B1 | 4/2003 |
| EP | 812167 B1 | 5/2003 |
| EP | 1308132 A2 | 5/2003 |
| EP | 703757 B1 | 8/2003 |
| EP | 855887 B1 | 8/2003 |
| EP | 1221914 B1 | 9/2003 |
| EP | 1219248 A3 | 1/2004 |
| EP | 1219268 A3 | 1/2004 |
| EP | 1344509 A3 | 2/2004 |
| EP | 1391188 A1 | 2/2004 |
| EP | 831759 B1 | 3/2004 |
| EP | 1405602 A1 | 4/2004 |
| EP | 1129668 B1 | 5/2004 |
| EP | 901351 B1 | 8/2004 |
| EP | 836457 B1 | 9/2004 |
| EP | 732093 B1 | 11/2004 |
| EP | 814718 B1 | 11/2004 |
| EP | 1197181 B1 | 11/2004 |
| EP | 1124510 B1 | 12/2004 |
| EP | 1488755 A1 | 12/2004 |
| EP | 1508307 A1 | 2/2005 |
| EP | 988003 B1 | 5/2005 |
| EP | 1346695 B1 | 12/2005 |
| EP | 1605836 A1 | 12/2005 |
| EP | 1221915 B1 | 2/2006 |
| EP | 1389983 B1 | 8/2006 |
| EP | 1684675 A1 | 8/2006 |
| EP | 1009338 B1 | 10/2006 |
| EP | 1709920 A3 | 10/2006 |
| EP | 1722722 A1 | 11/2006 |
| EP | 1374806 B1 | 12/2006 |
| EP | 1525863 A3 | 1/2007 |
| EP | 1762202 A2 | 3/2007 |
| EP | 1764066 A1 | 3/2007 |
| EP | 840580 B1 | 4/2007 |
| EP | 1009337 B1 | 6/2007 |
| EP | 1514519 A3 | 7/2007 |
| EP | 1618848 B1 | 7/2007 |
| EP | 1442732 B1 | 9/2007 |
| EP | 1829486 A1 | 9/2007 |
| EP | 1841385 A1 | 10/2007 |
| EP | 1153574 B1 | 2/2008 |
| EP | 1905390 A2 | 4/2008 |
| EP | 1905391 A1 | 4/2008 |
| EP | 1302182 B1 | 8/2008 |
| EP | 1437105 B1 | 10/2008 |
| EP | 1905931 B1 | 12/2008 |
| EP | 2016924 A3 | 4/2009 |
| EP | 2058014 A1 | 5/2009 |
| EP | 1829503 B1 | 9/2009 |
| EP | 1383449 B1 | 11/2009 |
| EP | 1439773 B1 | 1/2010 |
| EP | 1437988 B1 | 3/2010 |
| EP | 1500372 B1 | 3/2010 |
| EP | 1596764 B1 | 3/2010 |
| EP | 1549259 B1 | 4/2010 |
| EP | 1400221 B1 | 9/2011 |
| EP | 1833428 B1 | 4/2012 |
| EP | 1653892 B1 | 4/2013 |
| FR | 2703580 A1 | 10/1994 |
| FR | 2736537 A1 | 1/1997 |
| FR | 2738475 A1 | 3/1997 |
| FR | 2817463 A1 | 6/2002 |
| FR | 2841125 A1 | 12/2003 |
| FR | 2874814 A1 | 3/2006 |
| FR | 2948277 A1 | 1/2011 |
| JP | 2006-508714 A | 3/2006 |
| JP | 2006-516456 A | 7/2006 |
| JP | 2007-501027 A | 1/2007 |
| JP | 2007-517539 A | 7/2007 |
| JP | 2010-538683 A | 12/2010 |
| WO | 89/09035 A1 | 10/1989 |
| WO | 90/00037 A1 | 1/1990 |
| WO | 92/014423 A1 | 9/1992 |
| WO | 93/01771 A1 | 2/1993 |
| WO | 95/08964 A2 | 4/1995 |
| WO | 95/15133 A1 | 6/1995 |
| WO | 95/20370 A1 | 8/1995 |
| WO | 95/26164 A1 | 10/1995 |
| WO | 95/32673 A1 | 12/1995 |
| WO | 96/27321 A2 | 9/1996 |
| WO | 96/27345 A2 | 9/1996 |
| WO | 96/39988 A2 | 12/1996 |
| WO | 96/40015 A1 | 12/1996 |
| WO | 96/40019 A1 | 12/1996 |
| WO | 96/40020 A1 | 12/1996 |
| WO | 97/14377 A1 | 4/1997 |
| WO | 97/20526 A1 | 6/1997 |
| WO | 97/37620 A1 | 10/1997 |
| WO | 98/01091 A1 | 1/1998 |
| WO | 98/17208 A2 | 4/1998 |
| WO | 98/034568 A1 | 8/1998 |
| WO | 98/56319 A1 | 12/1998 |
| WO | 99/09896 A1 | 3/1999 |
| WO | 99/09913 A2 | 3/1999 |
| WO | 99/060956 A1 | 12/1999 |
| WO | 99/063914 A1 | 12/1999 |
| WO | 00/24343 A1 | 5/2000 |
| WO | 0024327 A2 | 5/2000 |
| WO | 00/74605 A1 | 12/2000 |
| WO | 01/28465 A2 | 4/2001 |
| WO | 01/68005 A2 | 9/2001 |
| WO | 01/95838 A1 | 12/2001 |
| WO | 2002/003870 A1 | 1/2002 |
| WO | 02/17823 A1 | 3/2002 |
| WO | 2003/003951 A1 | 1/2003 |
| WO | 03/32802 A2 | 4/2003 |
| WO | 2004/000176 A1 | 12/2003 |
| WO | 2004/000177 A1 | 12/2003 |
| WO | 2004/069033 A2 | 8/2004 |
| WO | 2004/080316 A1 | 9/2004 |
| WO | 2005/011539 A2 | 2/2005 |
| WO | 2005/041825 A1 | 5/2005 |
| WO | 2005/087143 A1 | 9/2005 |
| WO | 2005/094297 A2 | 10/2005 |
| WO | 2006/044920 A2 | 4/2006 |
| WO | 2006/072941 A2 | 7/2006 |
| WO | 2006/079356 A1 | 8/2006 |
| WO | 2006/118944 A1 | 11/2006 |
| WO | 2007/016801 A1 | 2/2007 |
| WO | 2007/048012 A2 | 4/2007 |
| WO | 2007/070751 A1 | 6/2007 |
| WO | 2007/093900 A2 | 8/2007 |
| WO | 2008/036636 A2 | 3/2008 |
| WO | 2008/079953 A3 | 10/2008 |
| WO | 2010/011348 A1 | 1/2010 |
| WO | 2010/075555 A2 | 7/2010 |
| WO | 2010/121002 A1 | 10/2010 |
| WO | 2011/013047 A2 | 2/2011 |
| WO | 2011/056172 A1 | 5/2011 |
| WO | 2011/060087 A1 | 5/2011 |
| WO | 2012/027490 A2 | 3/2012 |
| WO | 2012103254 A2 | 8/2012 |
| WO | 2012/129197 A1 | 9/2012 |
| WO | 2013/149611 A1 | 10/2013 |

OTHER PUBLICATIONS

Al-Sanabani, Application of Calcium Phosphate Materials in Dentistry, vol. 2013, Int. J. Biomaterials, 1-12, 2013.

(56) References Cited

OTHER PUBLICATIONS

Bailey, Stabilzation of the Cervical Spine by Anterior Fusion, 42-A(4), J. Bone Joint Surg., 565-594, Jun. 1960.
Banward, Iliac Crest Bone Graft Harvest Donor Site Morbidity, 20(9) Spine 1055-1060, May 1995.
Benezech, L'arthrodese Cervicale Par Voie Anterieure a L'Aide de Plaque-Cage P.C.B., 9(1) Rachis 1, 47, 1997 (w/ Translation).
Brantigan 1/F Cage for PLIF Surgical Technique Guide; Apr. 1991, 22 pages.
Brantigan, A Carbon Fiber Implant to Aid Interbody Lumbar Fusion, 16(6S) Spine S277-S282, Jul. 1991.
Brantigan, Compression Strength of Donor Bone for Posterior Lumbar Interbody Fusion, 18(9) Spine 1213-1221, 1993.
Brantigan, Interbody Lumbar Fusion Using a Carbon Fiber Cage Implant Versus Allograft Bone, 19(13) Spine 1436-1444, 1994.
Brantigan, Intervertebral Fusion, Chapter 27, Posterior Lumbar Interbody Fusion Using the Lumbar Interbody Fusion Cage, 437-466, 2006.
Brantigan, Pseudarthrosis Rate After Allograft Posterior Lumbar Interbody Fusion with Pedicle Screw and Plate Fixation, 19(11) Spine 1271-1280, Jun. 1994.
Carbon Fiber Composite Ramps for Lumbar Interbody Fusion; Apr. 1997, 2 pages.
Cloward, Gas-Sterilized Cadaver Bone Grafts for Spinal Fusion Operations, 5(1) Spine 4-10 Jan./Feb. 1980.
Cloward, The Anterior Approach for Removal of Ruptured Cervical Disks, vol. 15, J. Neuro. 602-617, 1958.
Dabrowski, Highly Porous Titanium Scaffolds for Orthopaedic Applications, J. Biomed Mater. Res. B. Appl. Biomat. Oct.;95(1):53-61, 2010.
Delecrin, Morbidite du Prelevement de Greffons osseuz au Niveau des Cretes Iliaques dans la Chirurgie Du Rachis; Justification du recours aux substituts osseuz, 13(3) Rachis 167-174, 2001 (w/Translation).
DePuy Motech Surgical Titanium Mesh Brochure; 1998, 13 pages.
Dereymaeker, Nouvelle Cure neuro-Chirurgicale de discopathies Cervicales, 2 Neurochirurgie 226-234; 1956 (w/ Translation).
Dickman, Internal Fixation and Fusion of the Lumbar Spine Using Threaded Interbody Cages, 13(3) Barrow Quarterly (1997); http://www.thebarrow.org/Education_And_Resources/Barrow_Quarterly/204837.
Enker, Interbody Fusion and Instrumentation, No. 300 Clin. Orth. Rel. Res. 90-101, Mar. 1994.
Fassio, Use of Cervical Plate-Cage PCB and Results for Anterior Fusion in Cervical Disk Syndrome, 15(6) Rachis 355-361, Dec. 2003 Translation.
Fowler, Complications Associated with Harvesting Autogenous Iliac Bone Graft, 24(12) Am. J. Ortho. 895-904, Dec. 1995.
Fuentes, Les Complications de la Chirurgie Par Voie Anterieure du Rachis Cervical, 8(1) Rachis 3-14, 1996 (w/ Translation).
Germay, Resultats Cliniques de Ceramiques D'hydroxyapatite dans les arthrodeses Inter-somatiques du Rachis Cervical Par Voie Anterieure. Etude Retrospective a Propose de 67 cas. 13(3), Rachis 189-195, 2001 (w/Translation).
Graham, Lateral Extracavitary Approach to the Thoracic and Thoracolumbar Spine, 20(7) Orthopedics, 605-610, Jul. 1997.
Gunatillake, Biodegradable Synthetic Polymers for Tissue Engineering, vol. 5, Eur. Cells Materials, 1-16, 2003.
Huttner, Spinal Stenosis & Posterior Lumbar Interbody Fusion, No. 193, Clinical Ortho Rel. Res. 103-114, Mar. 1985.
Jost, Compressive Strength of Interbody Cages in the Lumbar Spine: the Effect of Cage Shape, Posterior Instrumentation and Bone Density, 7 Eur. Spine J. 132-141, 1998.
Kastner, Advanced X-Ray Tomographic Methods for Quantitative Charecterisation of Carbon Fibre Reinforced Polymers, 4th Annual Intern. Symposium on NDT in Aerospace, 2012, 9 pages.
Khan, Chapter 2—Implantable Medical Devices, Focal Controlled Drug Delivery, Advances in Delivery Science and Technology, A.J. Domb and W. Khan (eds.) 2014.
Kozak, Anterior Lumbar Fusion Options, No. 300, Clin. Orth. Rel. Res., 45-51, 1994.

Kroppenstedt, Radiological Comparison of Instrumented Posterior Lumbar Interbody Fusion with One or Two Closed-Box Plasmapore Coated Titanium Cages, 33(19) Spine, 2083-2088, Sep. 2008.
Lund, Interbody Cage Stabilisation in the Lumbar Spine, 80(2) J Bone Joint Surg., 351-359, Mar. 1998.
Lyu, Degradability of Polymers for Implantable Biomedical Devices, 10, Int. J. Mal. Sci., 4033-4065, 2009.
Malca, Cervical Interbody Xenograft with Plate Fixation, 21(6) Spine, 685-690, Mar. 1996.
McAfee, Minimally Invasive Anterior Retroperitoneal Approach to the Lumbar Spine, 21(13) Spine, 1476-1484, 1998.
Nasca, Newer Lumbar Interbody Fusion Techniques, 22(2) J. Surg. Ortho. Advances, 113-117,2013.
PCB Evolution Surgical Technique Guide 2010.
Polysciences Inc. Info Sheet 2012.
Porex Website, http://www.porex.com/technologies/materials/porous-plastics, Porous Plastic Materials, accessed Aug. 21, 2015, 2 pages.
Samandouras, A New Anterior Cervical Instrumentation System Combining an Intradiscal Cage with an Integrated Plate, 26(10) Spine, 1188-1192, 2001.
Sonntag, Controversy in Spine Care, Is Fusion Necessary After Anterior Cervical Discectomy 21(9) Spine, 1111-1113, May 1996.
Supplementary EP Search Report for European Application 00980805 (EP1239796A4) dated Feb. 26, 2007, 3 pages.
Supplementary EP Search Report for European Application 01908625 (EP1416891A4) dated Dec. 15, 2006, 4 pages.
Supplementary EP Search Report for European Application 03749686 (EP1555966A4) dated Feb. 3, 2011, 3 pages.
Supplementary EP Search Report for European Application 03752374 (EP1549259A4) dated Mar. 20, 2007, 4 pages.
Supplementary EP Search Report for European Application 03786692 (EP1570222A4) dated Sep. 19, 2008, 2 pages.
Supplementary EP Search Report for European Application 03813779 (EP1587460A4) dated Nov. 4, 2010, 4 pages.
Synthes History and Evolution of LBIF Brochure; Nov. 2015, 30 pages.
Synthes Spine Cervical Stand-Alone Devices Presentation Brochure; 2010, 40 pages.
Synthes Spine, "OPAL Spacer System. Oblique posterior atraumatic lumbar spacer system, Technique Guide" (Brochure), 2008, US.
Synthes Spine, "T-PLIF Spacer Instruments, Technique Guide", (Brochure), 2001, US.
Synthes Spine, "Vertebral Spacer—TR" (Brochure), 2002, US.
Synthes Spine, "Vertebral Spacer—PR", (Brochure), 2002, US.
Synthes Spine, "Vertebral Spacer—PR. Vertebral body replacement device intended for use in the thoracolumbar spine", (Brochure), 2002, US.
Takahama, A New Improved Biodegradable Tracheal Prosthesis Using Hydroxy Apatite and Carbon Fiber 35(3) ASAIO Trans, 291-293, Jul.-Sep. 1989.
Tamariz, Biodegradation of Medical Purpose Polymeric Materials and Their Impact on Biocompatibility, Chapter 1, Intech-bio degradation Life of Science, 2013; 28 pages.
Tan, A Modified Technique of Anterior Lumbar Fusion with Femoral Cortical Allograft, 5(3) J. Ortho. Surg. Tech., 83-93, 1990.
Verbiest H., La Chirurgie Anterieure et Laterale du Rachis Cervical,16(S2) Neurochirurgie 1-212; 1970 (w/ Translation).
Wang, Determination of Cortical Bone Porosity and Pore Size Distribution using a Low Field Pulsed NMR Approach, J. Orthop Res., Mar.; 21(2):312-9 Mar. 2003.
Wang, Increased Fusion Rates with Cervical Plating for Two-Level Anterior Cervical Discectomy and Fusion, 25(1) Spine 41-45, Jan. 2000.
Watters, Anterior Cervical Discectomy with and without Fusion, 19(20) Spine 2343-2347 Oct. 1994.
Weiner, Spindle Update Lumbar Interbody Cages, 23(5) Spine, 634-640, Mar. 1998.
White, Relief of Pain by Anterior Cervical-Spine Fusion for Spondylosis, 55-A(3) J. Bone Joint Surg. 525-534, Apr. 1973.
Whitesides, Lateral Approach to the Upper Cervical Spine for Anterior Fusion, vol. 59, South Med J, 879-883, Aug. 1966.
Wilson, Anterior Cervical Discectomy without Bone Graft, 47(4) J. Neurosurg. 551-555, Oct. 1977.

(56) References Cited

OTHER PUBLICATIONS

Younger, Morbidity at Bone Graft Donor Sites, 3(3) J. Orth. Trauma, 192-195, 1989.
U.S. Appl. No. 16/103,136, filed Aug. 14, 2018, Intervertebral Implant Inserters and Related Methods.

* cited by examiner

Detail A

Section A-A

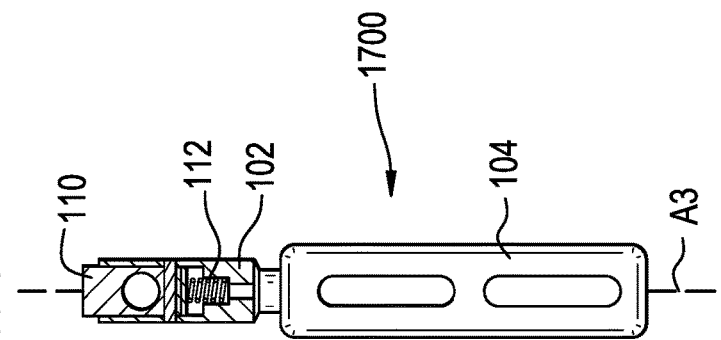
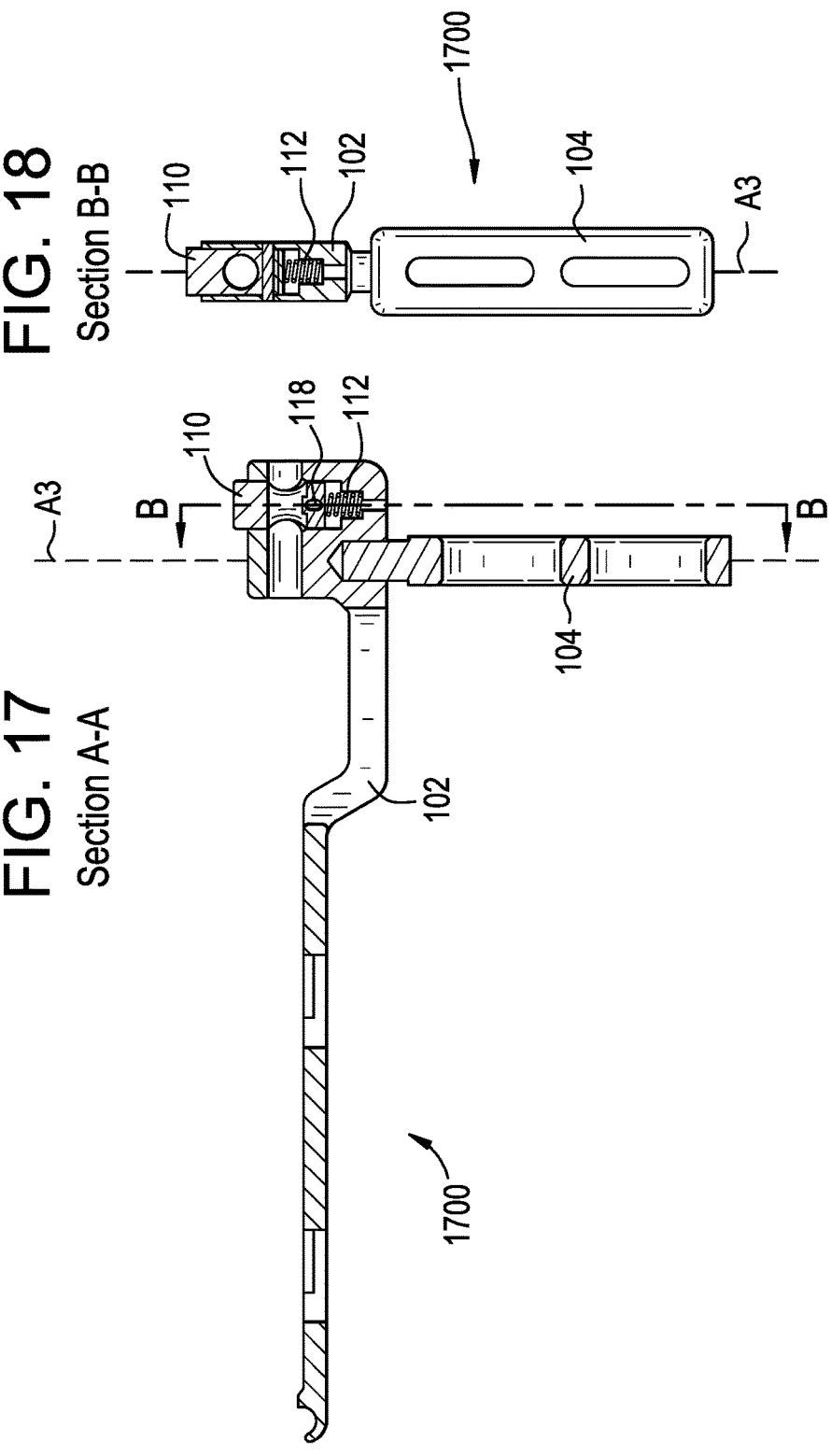
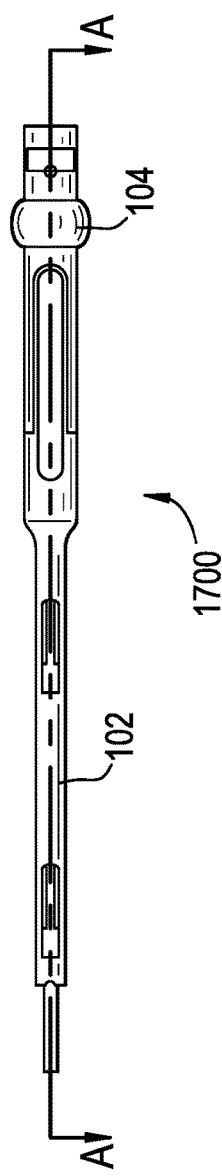

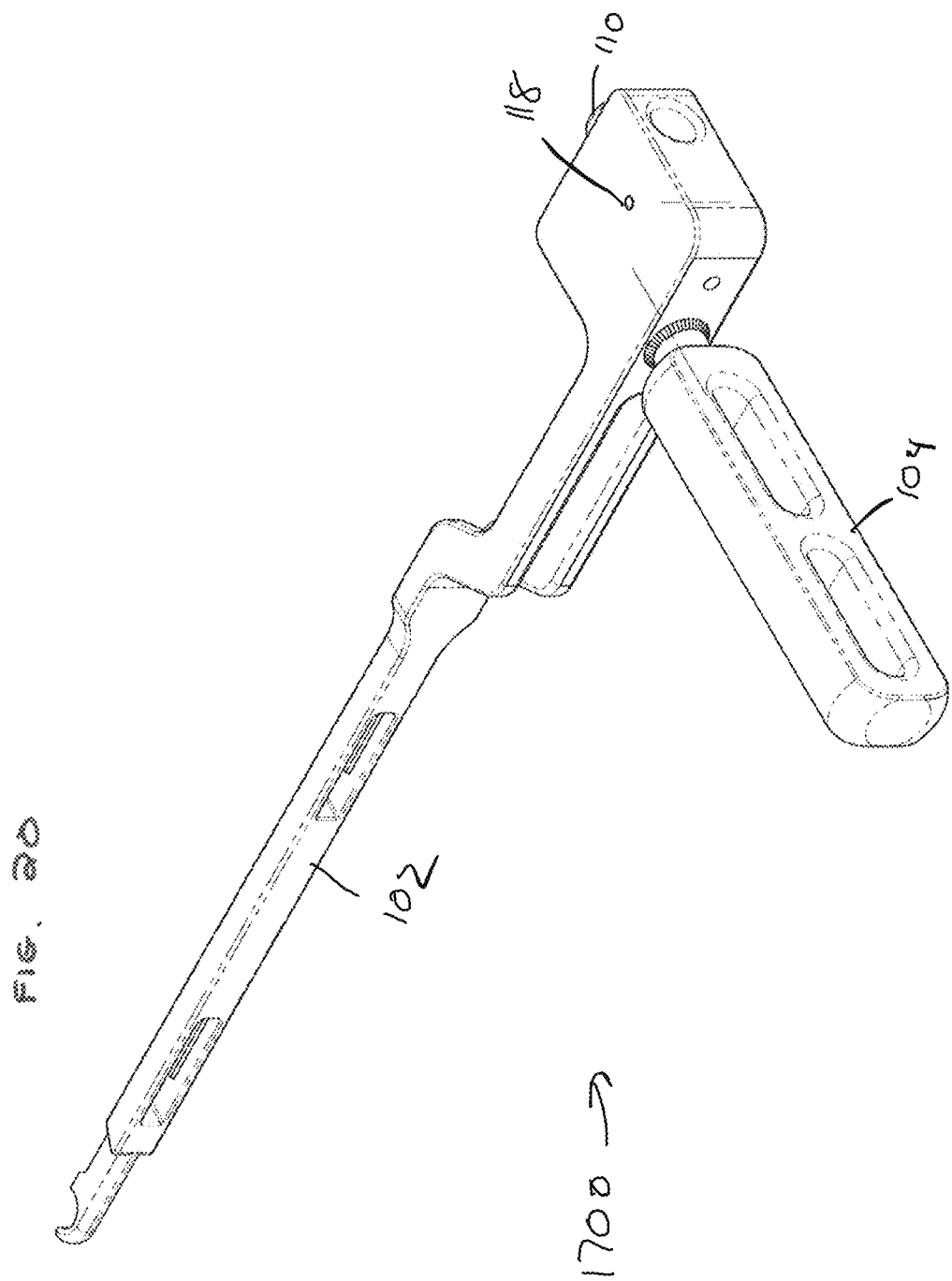

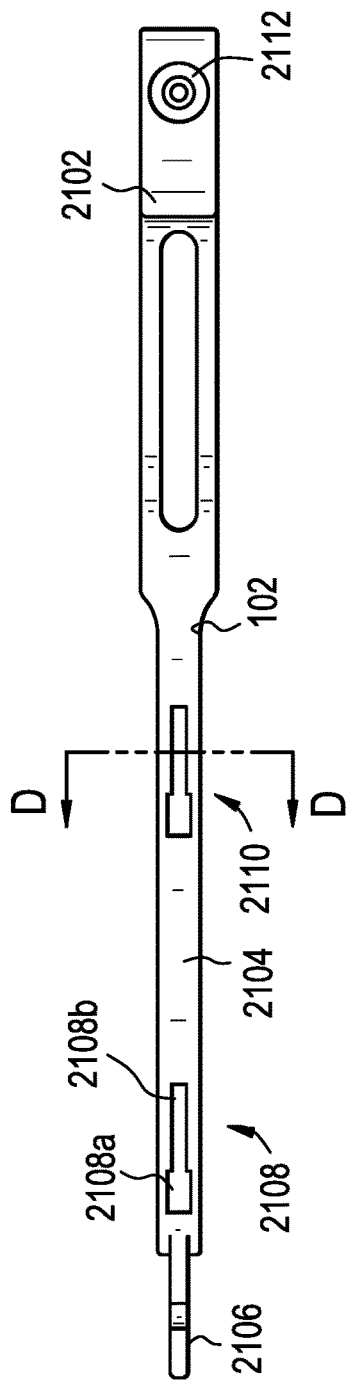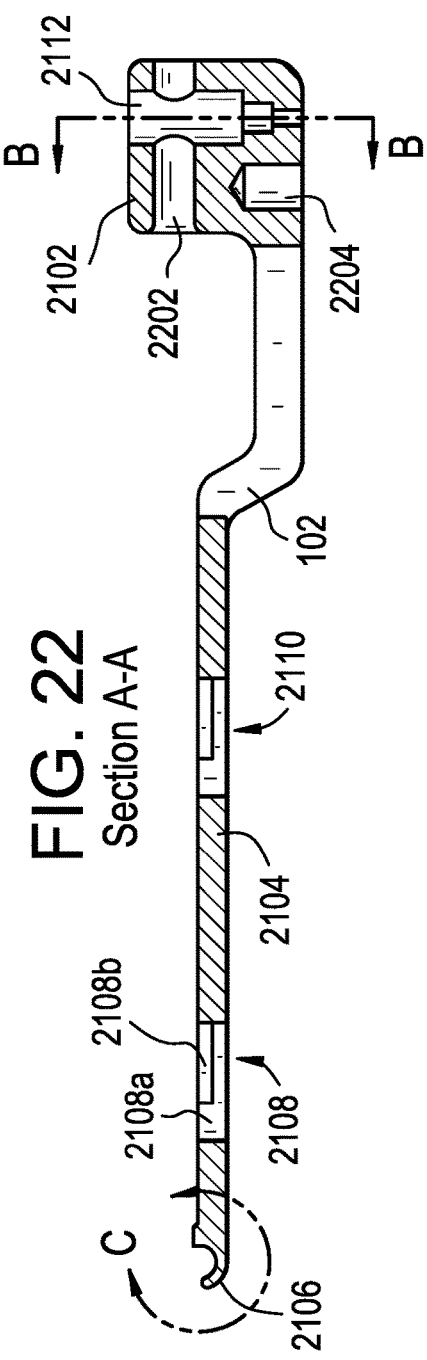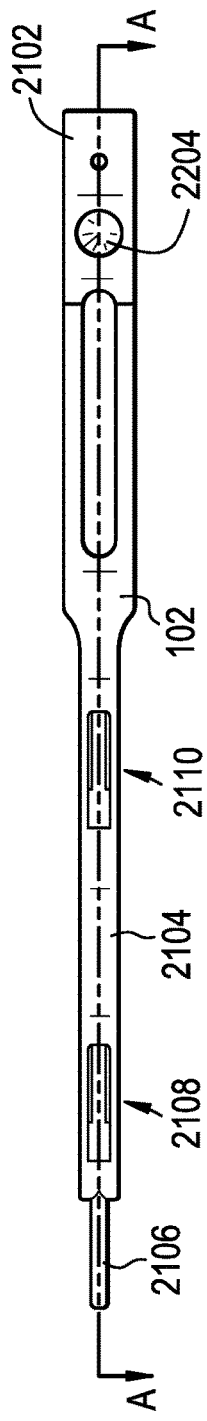

SECTION B-B

SECTION D-D

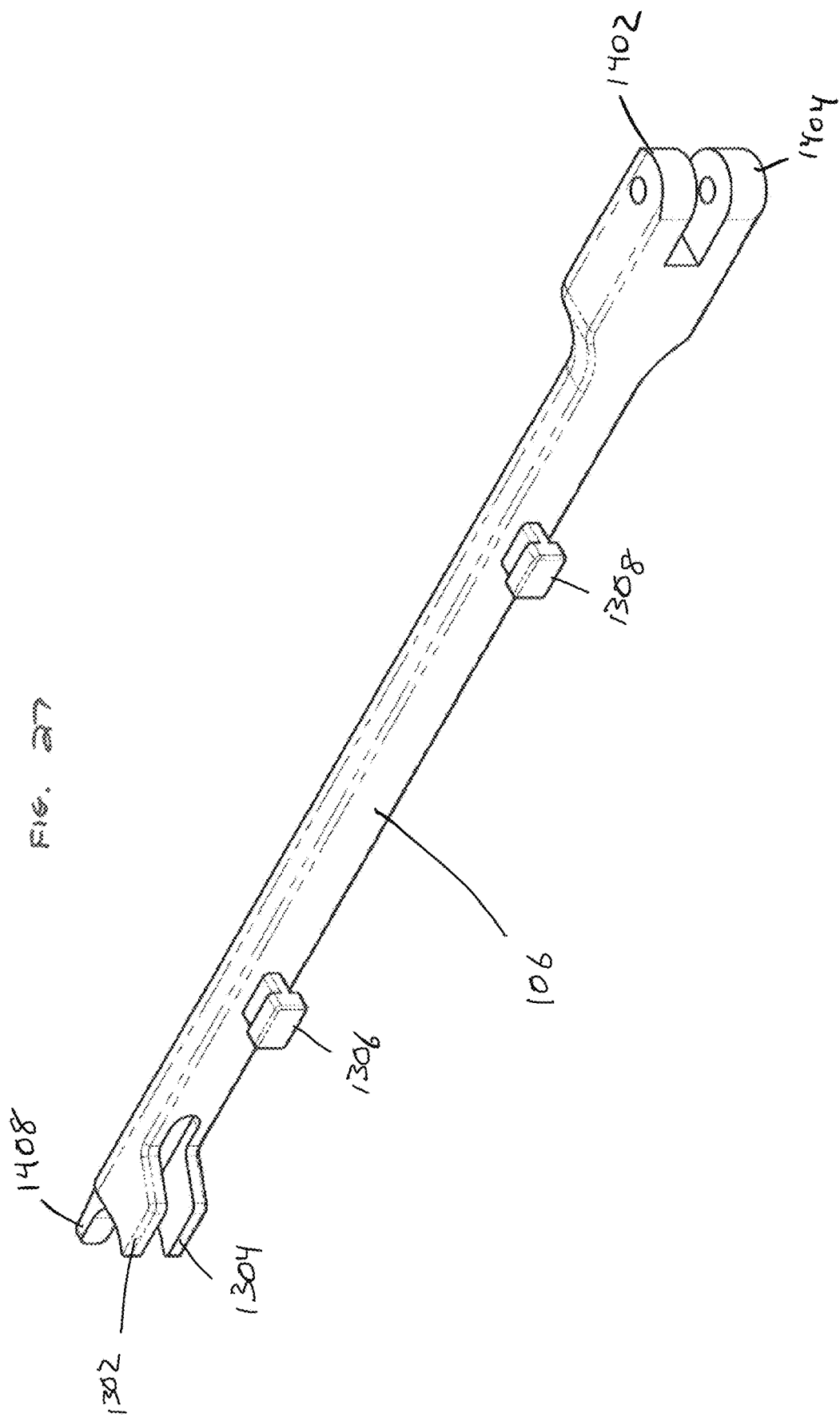

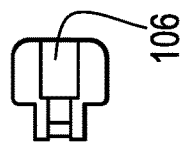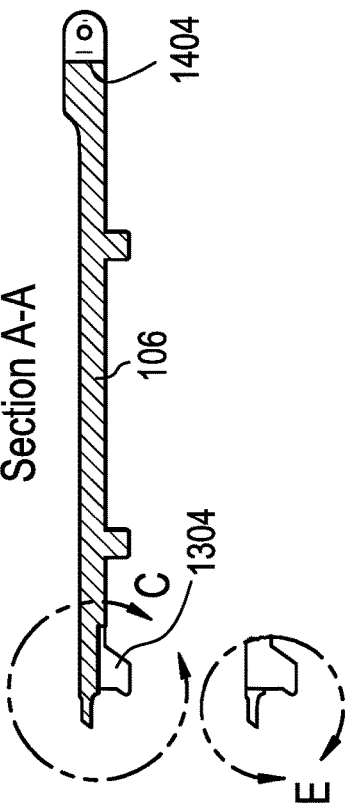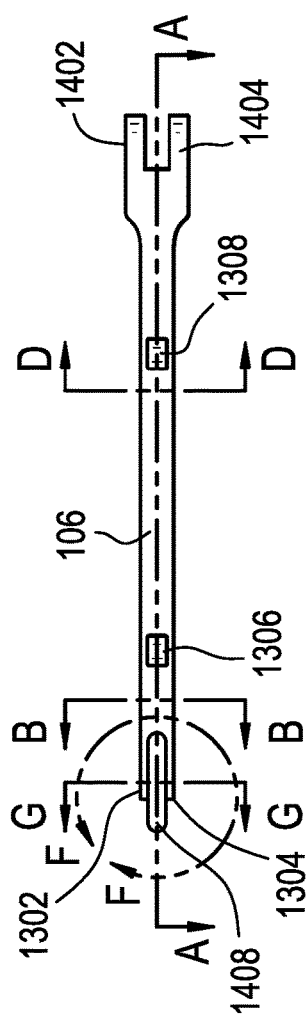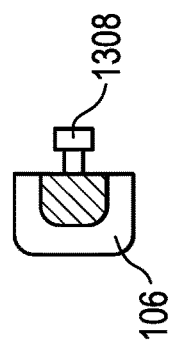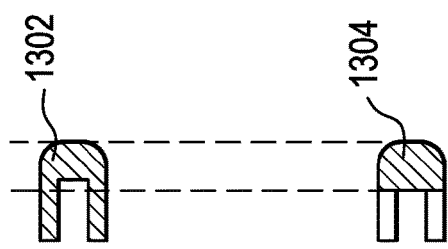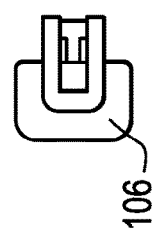

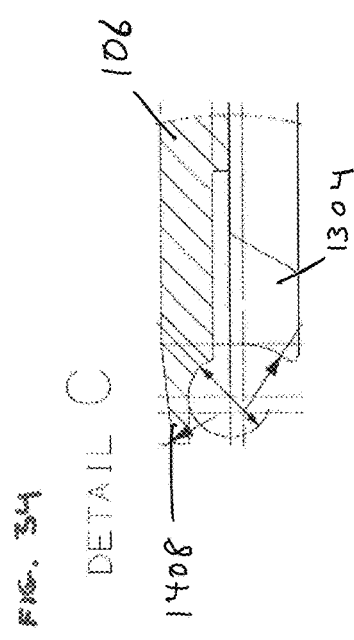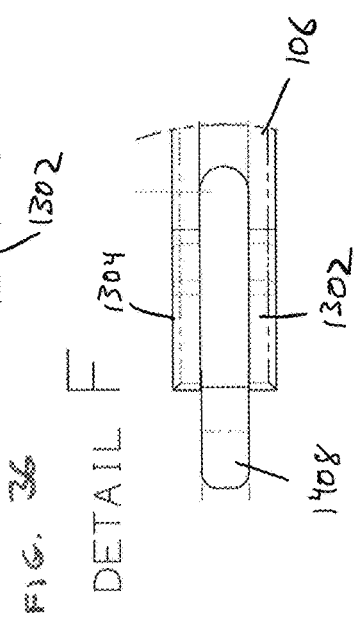

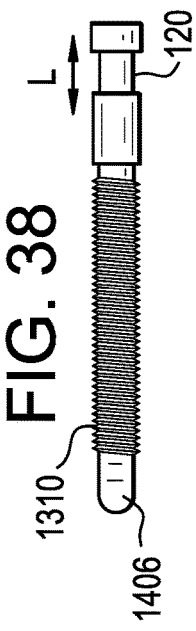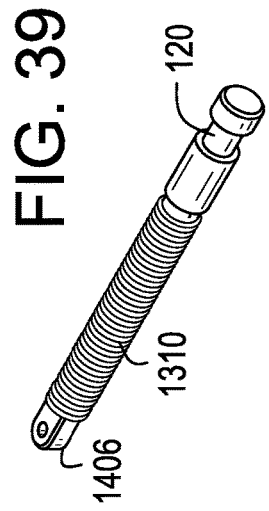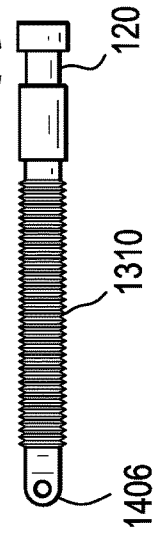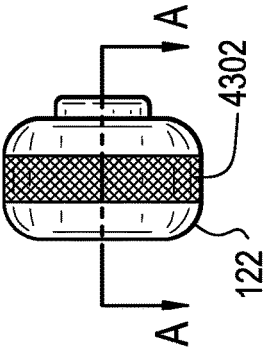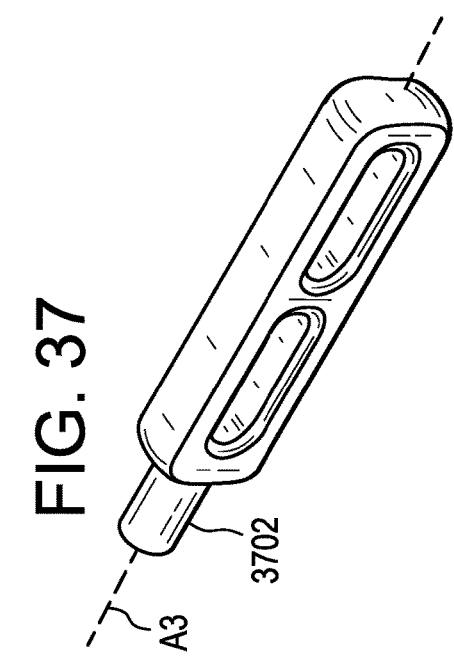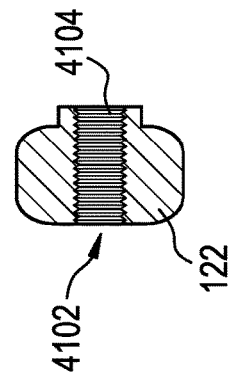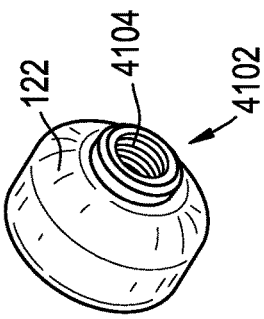

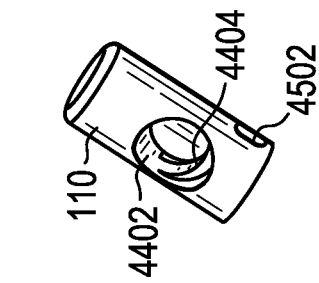
FIG. 48
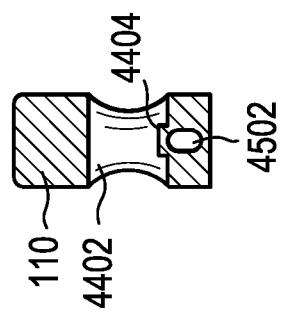
FIG. 47
Section B-B
FIG. 51
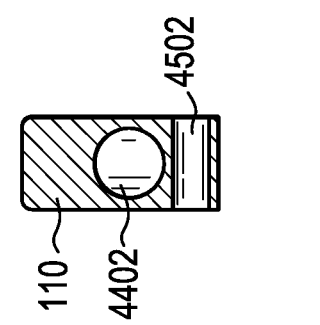
FIG. 46
Section A-A
FIG. 50
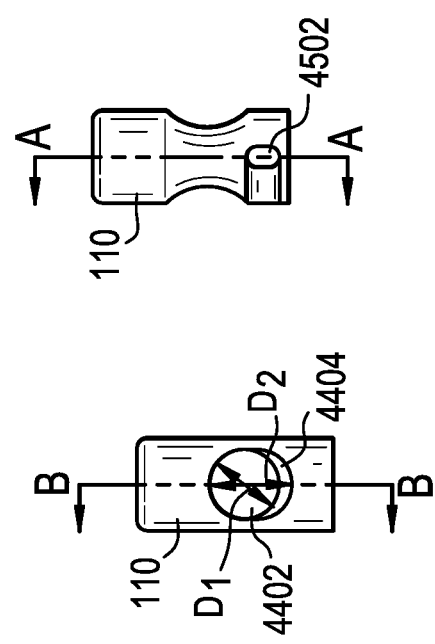
FIG. 45
FIG. 44
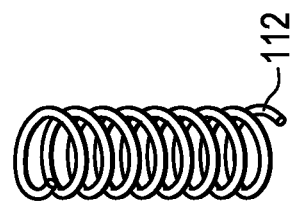
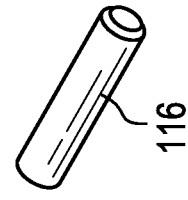
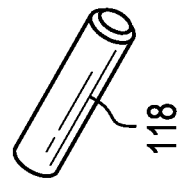
FIG. 49

IMPLANT INSERTERS AND RELATED METHODS

CROSS-REFERENCE TO RELATED APPLICATIONS

This application claims the benefit of U.S. Provisional Application No. 62/534,039, filed Jul. 18, 2017, the entire contents of which are incorporated herein by reference.

FIELD

Implant inserters and related methods are disclosed herein, e.g., for delivering a fusion cage or other implant to a spinal disc space and for rotating or articulating the implant within the disc space.

BACKGROUND

There are a number of surgical procedures in which an implant is delivered to a location within a patient. In spine surgery, for example, a fusion cage, disc prosthesis, or other implant may be delivered to a disc space defined between two vertebrae. Insertion and proper positioning of the implant can be challenging for the surgeon, particularly when the implant is delivered through a narrow working channel, e.g., in the case of minimally-invasive approaches to the spine.

By way of further example, in some procedures it can be necessary to insert an implant in a first orientation and subsequently manipulate the implant into a second orientation after insertion. When inserting through a narrow working channel, for example, it can be necessary to insert an implant such that its smallest cross-sectional area faces distally or in the direction of insertion. Once through a narrow working channel and within a patient, however, it can be necessary to manipulate the implant into a different orientation for optimal or intended performance. In some cases, it can also be desirable to perform such manipulation of an implant without releasing the implant from an inserter in case additional manipulation, removal, or other revision is required to properly position the implant.

Accordingly, there is a need for improved implant inserters and related methods that can facilitate insertion and proper positioning of an implant within a patient.

SUMMARY

Implant inserters and related methods are disclosed herein, e.g., for delivering a fusion cage or other implant to a spinal disc space and for rotating or articulating the implant within the disc space. An exemplary instrument can include a slider that is slidably mounted to a body to define an implant clamp. A locking mechanism can allow the slider to be quickly disassembled from the body and for fast and convenient loading and unloading of an implant to the instrument. An actuation knob can be moved between a first position in which the implant is locked from rotating relative to the instrument and a second position in which the implant is retained to the instrument but allowed to rotate relative to the instrument.

In one aspect, a surgical instrument is provided that includes a proximal end, a distal end, a central longitudinal axis extending between the proximal and distal ends, a body, a slider coupled to the body. The body and the slider collectively define an implant clamp at the distal end of the instrument. The instrument further includes an actuation knob movable between a first position in which the clamp is configured to retain an implant to the instrument without allowing the implant to rotate relative to the instrument and a second position in which the clamp is configured to retain an implant to the instrument while allowing the implant to rotate relative to the instrument.

The devices and methods described herein can have a number of additional features and/or variations, all of which are within the scope of the present disclosure. In some embodiments, for example, the clamp can be configured to selectively allow rotation of the implant about a rotation axis that is perpendicular to the central longitudinal axis. In some embodiments, the instrument can further include a handle extending from the body such that a central longitudinal axis of the handle is transverse to the central longitudinal axis of the instrument. In such embodiments, the rotation axis can be perpendicular to a plane defined by the central longitudinal axis of the instrument and the central longitudinal axis of the handle.

In certain embodiments, the instrument can further include a locking shaft coupled to a proximal end of the slider, and a proximal end of the locking shaft can include a groove formed therein and a central portion of the locking shaft can include exterior threads formed thereon. Further, the locking shaft can be received within a first bore formed in the body. In some embodiments, the actuation knob can include a central opening having interior threads that mate with the exterior threads formed on the locking shaft.

In other embodiments, the instrument can further include an actuator disposed within a second bore formed in the body and configured to move between a first position to couple the locking shaft to the body and a second position to release the locking shaft from the body. In some embodiments, the actuator can be biased toward the first position. In certain embodiments, the actuator can be configured to couple the locking shaft to the body by disposing a portion thereof within the groove formed in the locking shaft. Further, the groove in the locking shaft can be sized such that some degree of proximal and distal translation of the locking shaft relative to the actuator and the body is possible when the actuator is in the first position.

In another aspect, a surgical method is provided that includes coupling an implant to an inserter such that the implant cannot rotate relative to the inserter and passing the implant through a working channel to a surgical site. The method also includes configuring the inserter to allow rotation of the implant relative to the inserter while still retaining the implant to the inserter, articulating the implant while retained to the inserter, and releasing the implant from the inserter.

As with the above-described aspect, a number of additional features and/or variations can be included, all of which are within the scope of the present disclosure. In some embodiments, for example, coupling the implant to the inserter can include moving an actuator of the inserter from a first position to a second position to allow a slider of the inserter to be withdrawn proximally relative to a body of the inserter and thereby open an implant clamp of the inserter defined by distal ends of the slider and the body.

In some embodiments, coupling the implant to the inserter can further include placing a portion of the implant within the implant clamp, advancing the slider distally relative to the body to close the implant clamp around the portion of the implant, moving the actuator to the first position to limit movement of the slider relative to the body, and rotating an actuation knob in a first direction to further advance the slider distally and lock the rotational position of the implant relative to the inserter.

In certain embodiments, configuring the inserter to allow rotation of the implant relative to the inserter while still retaining the implant to the inserter can include rotating the actuation knob in a second direction to retract the slider proximally relative to the body. Further, releasing the implant from the inserter can in some embodiments include moving the actuator from the first position to the second position and retracting the slider proximally relative to the body to open the implant clamp.

In another aspect, a surgical instrument is provided that includes a body having an elongate distal portion and a handle extending from a proximal portion of the body, as well as a slider coupled to the body and extending parallel to the elongate distal portion of the body. Distal ends of the slider and the body can collectively define an implant clamp. The instrument can further include a locking shaft coupled to a proximal end of the slider and received within a first bore formed in the proximal portion of the body, as well as a first actuator disposed within a second bore formed in the proximal portion of the body. The first actuator can be configured to selectively limit proximal and distal translation of the slider relative to the body. The instrument can further include a second actuator disposed about the locking shaft that is also configured to limit proximal and distal translation of the slider relative to the body. The first actuator and the second actuator can be configured to selectively retain an implant within the implant clamp and selectively allow rotation of the implant relative to the instrument.

In some embodiments, the clamp can be configured to selectively allow rotation of the implant about a rotation axis that is perpendicular to a central longitudinal axis of the instrument extending between a proximal end of the body and the distal end of the body. In certain embodiments, the handle can extend from the proximal portion of the body such that a central longitudinal axis of the handle is transverse to the central longitudinal axis of the instrument, and the rotation axis can be perpendicular to a plane defined by the central longitudinal axis of the instrument and the central longitudinal axis of the handle.

In some embodiments, the second actuator can be a knob including a central opening having interior threads that mate with the exterior threads formed on the locking shaft.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

The aspects and embodiments described above will be more fully understood from the following detailed description taken in conjunction with the accompanying drawings, in which:

FIG. 17 is a cross-sectional view of the body, handle, and push button of the implant inserter of FIG. 1 taken along the line A-A shown in FIG. 19;

FIG. 18 is a cross-sectional view of the components of FIG. 17 taken along the line B-B shown in FIG. 17;

FIG. 19 is a bottom view of the body and handle of the implant inserter of FIG. 1;

FIG. 20 is a perspective view of the body and handle of the implant inserter of FIG. 1;

FIG. 21 is a top view of the body of the implant inserter of FIG. 1;

FIG. 22 is a cross-sectional view of the body of the implant inserter of FIG. 1 taken along the line A-A shown in FIG. 23;

FIG. 23 is a bottom view of the body of the implant inserter of FIG. 1;

FIG. 27 is a perspective view of the slider of the implant inserter of FIG. 1;

FIG. 28 is a cross-sectional view of the slider of the implant inserter of FIG. 1 taken along the line G-G shown in FIG. 31;

FIG. 29 is a cross-sectional view of the slider of the implant inserter of FIG. 1 taken along the line A-A shown in FIG. 31;

FIG. 30 is a cross-sectional view of the slider of the implant inserter of FIG. 1 taken along the line B-B shown in FIG. 31;

FIG. 31 is a bottom view of the slider of the implant inserter of FIG. 1;

FIG. 32 is a rear view of the slider of the implant inserter of FIG. 1;

FIG. 33 is a cross-sectional view of the slider of the implant inserter of FIG. 1 taken along the line D-D shown in FIG. 31;

FIG. 34 is a detail cross-sectional view of the portion of the slider circled C in FIG. 29;

FIG. 35 is a detail view of the portion of the slider circled E in FIG. 29;

FIG. 36 is a detail view of the portion of the slider circled F in FIG. 31;

FIG. 37 is a perspective view of the handle of the implant inserter of FIG. 1;

FIG. 38 is a top view of the locking shaft of the implant inserter of FIG. 1;

FIG. 39 is a perspective view of the locking shaft of the implant inserter of FIG. 1;

FIG. 40 is a side view of the locking shaft of the implant inserter of FIG. 1;

FIG. 41 is a cross-sectional view of the actuation knob of the implant inserter of FIG. 1 taken along the line A-A shown in FIG. 43;

FIG. 42 is a perspective view of the actuation knob of the implant inserter of FIG. 1;

FIG. 43 is a side view of the actuation knob of the implant inserter of FIG. 1;

FIG. 44 is a front view of the push button of the implant inserter of FIG. 1;

FIG. 45 is a side view of the push button of the implant inserter of FIG. 1;

FIG. 46 is a cross-sectional view of the push button of the implant inserter of FIG. 1 taken along the line A-A shown in FIG. 45;

FIG. 47 is a cross-sectional view of the push button of the implant inserter of FIG. 1 taken along the line B-B shown in FIG. 44;

FIG. 48 is a perspective view of the push button of the implant inserter of FIG. 1;

FIG. 49 is a perspective view of the spring of the implant inserter of FIG. 1;

FIG. 50 is a perspective view of the first pin of the implant inserter of FIG. 1;

FIG. 51 is a perspective view of the second pin of the implant inserter of FIG. 1.

DETAILED DESCRIPTION

Implant inserters and related methods are disclosed herein, e.g., for delivering a fusion cage or other implant to a spinal disc space and for rotating or articulating the implant within the disc space. An exemplary instrument can include a slider that is slidably mounted to a body to define an implant clamp. A locking mechanism can allow the slider to be quickly disassembled from the body and for fast and convenient loading and unloading of an implant to the instrument. An actuation knob can be moved between a first position in which the implant is locked from rotating relative to the instrument and a second position in which the implant is retained to the instrument but allowed to rotate relative to the instrument.

Certain exemplary embodiments will now be described to provide an overall understanding of the principles of the structure, function, manufacture, and use of the instruments and methods disclosed herein. One or more examples of these embodiments are illustrated in the accompanying drawings. Those skilled in the art will understand that the instruments and methods specifically described herein and illustrated in the accompanying drawings are non-limiting exemplary embodiments. The features illustrated or described in connection with one exemplary embodiment may be combined with the features of other embodiments.

Figure 1:
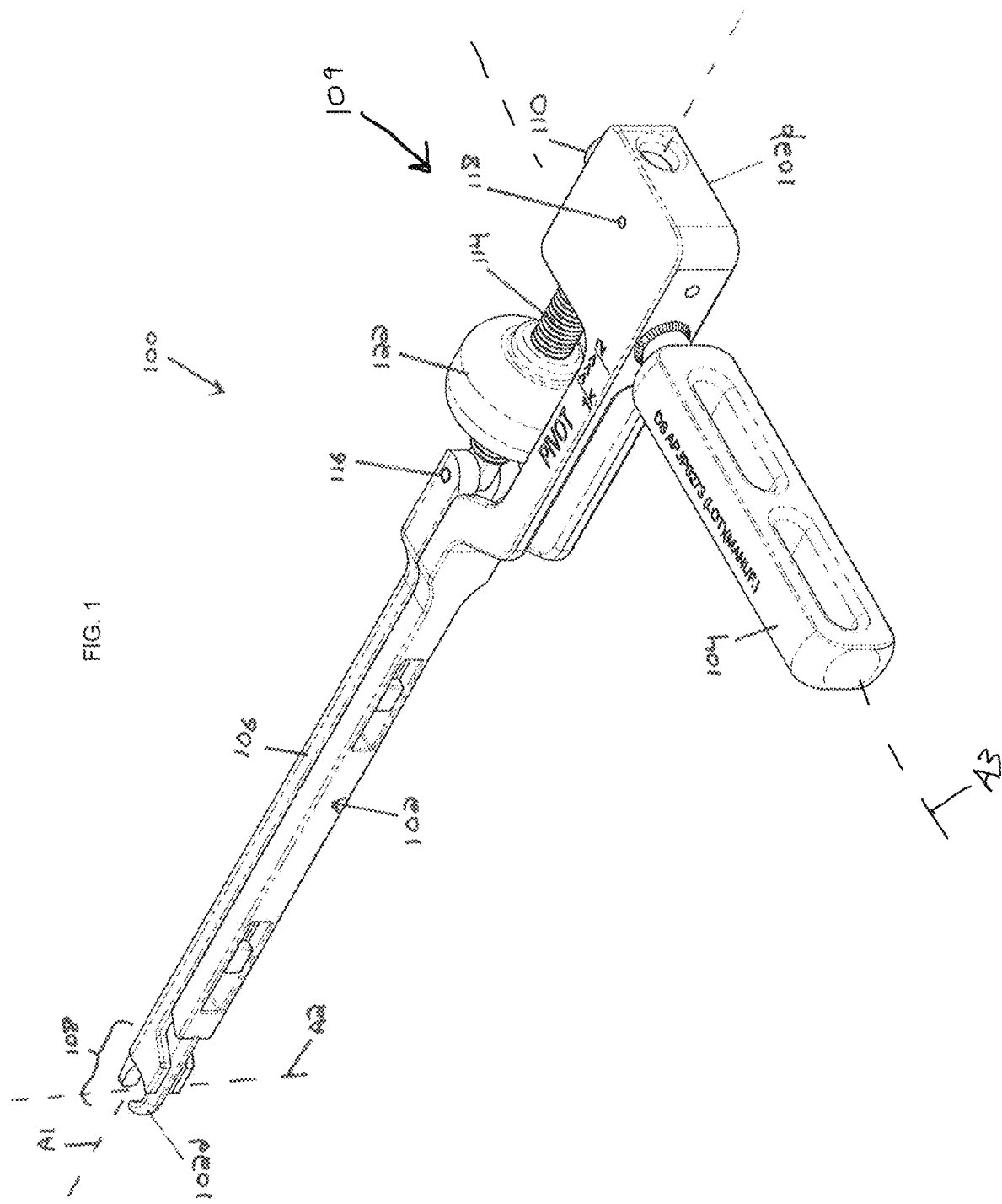
FIG. 1 illustrates a perspective view of one embodiment of an implant inserter.
Figure 2:
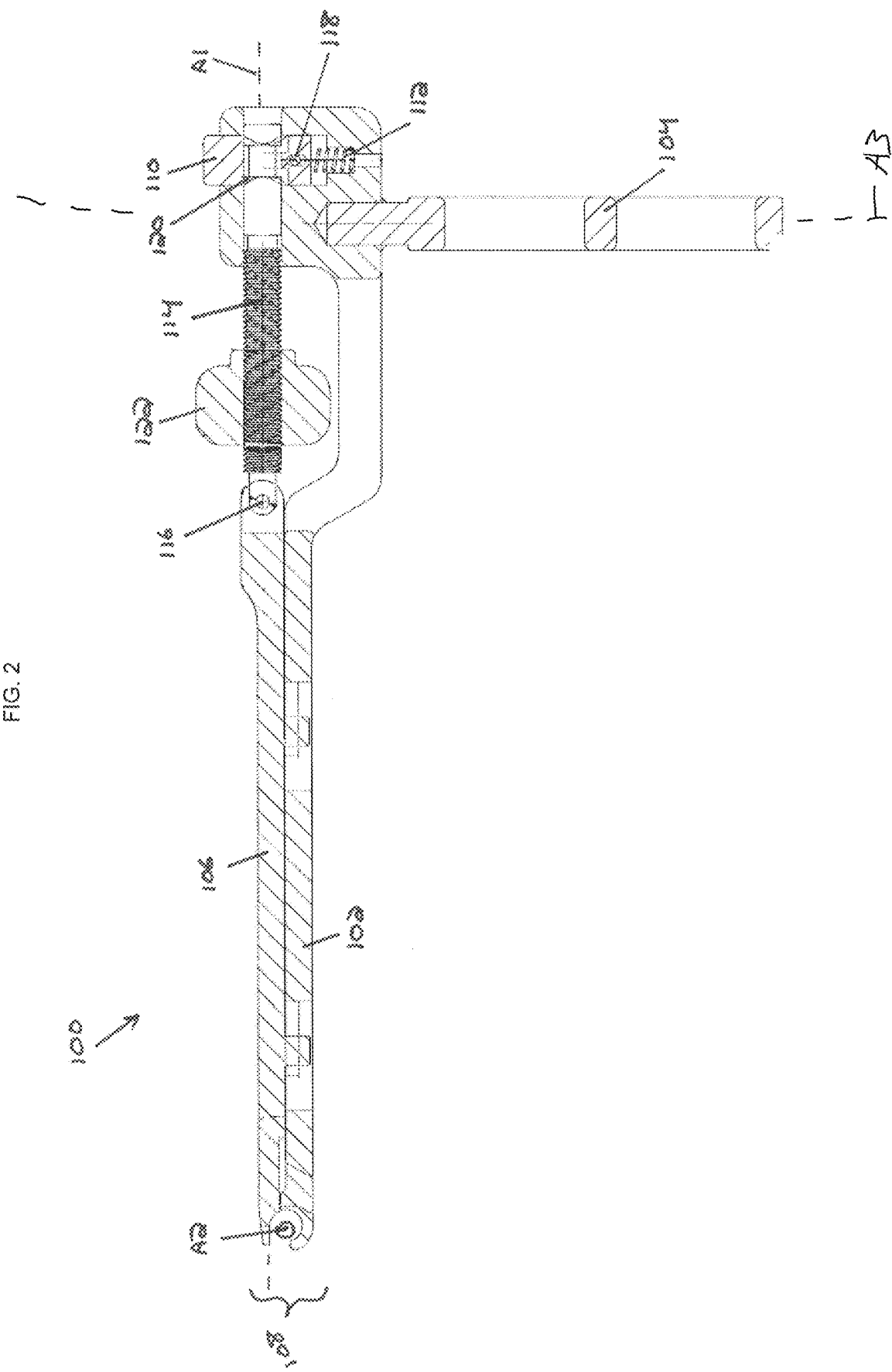
FIG. 2 illustrates side cross-sectional view of the implant inserter of FIG. 1.
Figure 3:
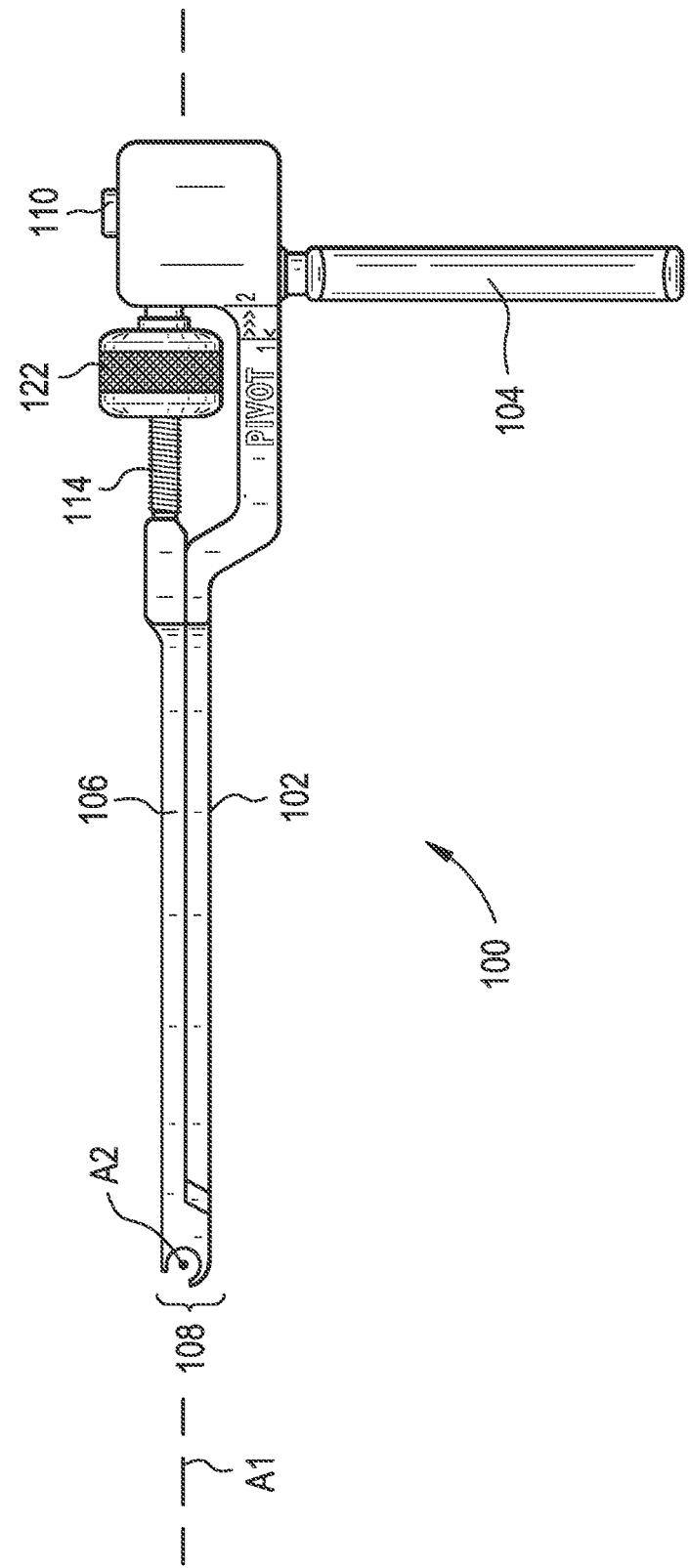
FIG. 3 illustrates a side view of the implant inserter of FIG. 1.
Figure 52:
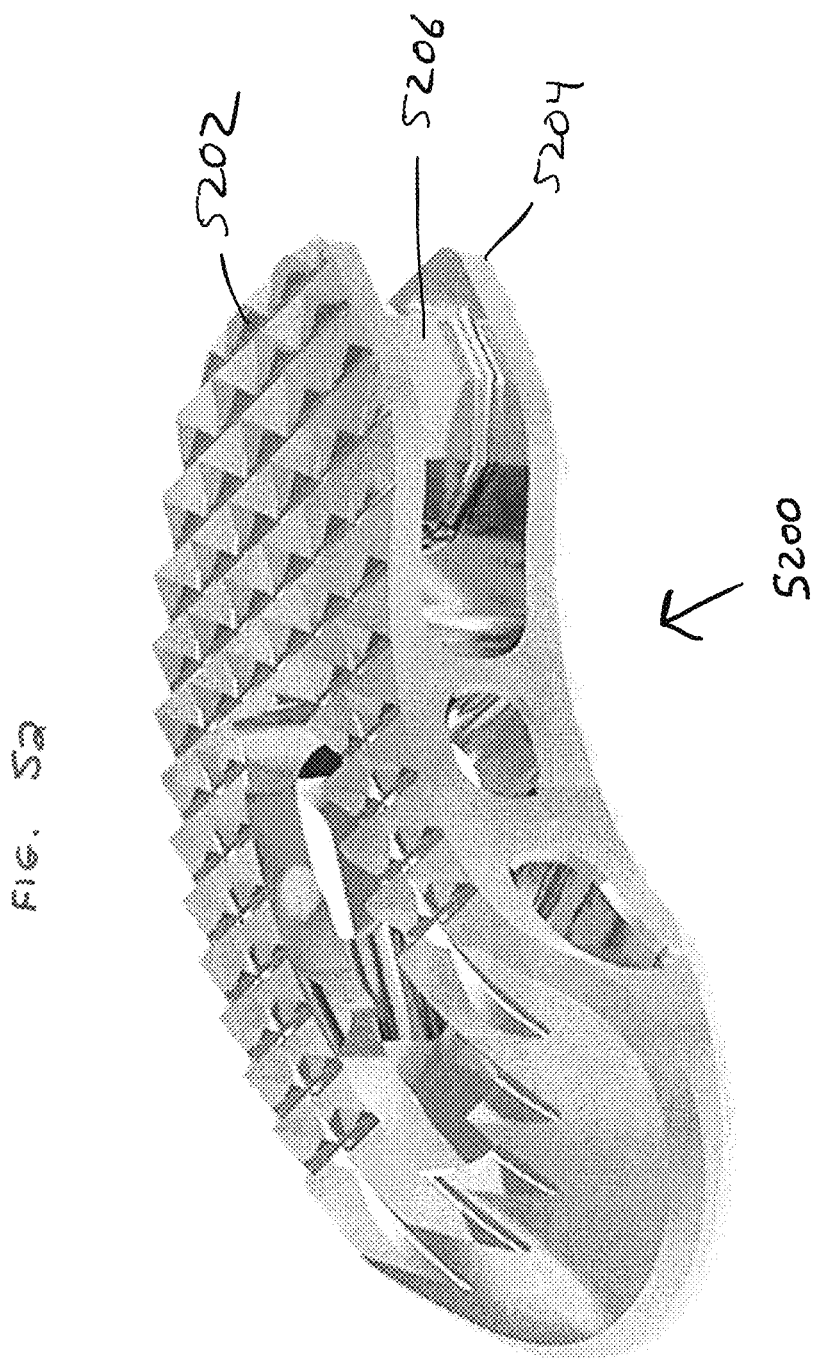
FIG. 52 illustrates an exemplary implant that can be inserted using the implant inserter.

FIGS. 1-3 illustrate an exemplary implant inserter instrument 100. The instrument 100 can be used to insert an implant into a target location within a patient, such as a spinal disc space. The instrument 100 can be used to articulate or rotate the implant, or to allow the implant to be articulated or rotated, while the implant is disposed in the target location, or as the implant is delivered to the target location. The instrument 100 can allow the implant to rotate relative to the instrument while the implant remains captured or retained by the instrument. Exemplary implants with which the instrument 100 can be used include the T-PAL TLIF spacer available from DEPUY SYNTHES SPINE of Raynham, Mass. An example of this implant 5200 is shown in FIG. 52.

The instrument 100 can include a body 102 that extends from a proximal end 102p to a distal end 102d along a central longitudinal axis A1 of the instrument 100. The body 102 can include a handle or grip 104 extending therefrom. A slider 106 can be slidably coupled to the body 102 such that the slider can translate along the axis A1 relative to the body. The distal ends of the slider 106 and the body 102 can collectively define an implant clamp 108 configured to selectively grasp, capture, and/or retain an implant. The clamp 108 can be configured to selectively hold an implant while permitting articulation of the implant about an axis A2. The axis A2 can be perpendicular to the axis A1 and can extend between superior and inferior bone-contacting surfaces of the implant.

The proximal end of the slider 106 can be coupled to the body 102 via a locking mechanism 109. The locking mechanism 109 can have a first position in which the locking mechanism does not restrict axial translation of the slider 106 relative to the body 102, and a second position in which the locking mechanism limits axial translation of the slider relative to the body. The locking mechanism 109 can include a push button or other actuator 110 biased by a spring or other biasing element 112 and a locking shaft 114 disposed through an aperture formed in the button. The locking shaft 114 can be pivotally coupled to the slider 106 by a first pin 116. The button 110 can be slidably retained to the body 102 by a second pin 118. Pressing the button 110 into the body 102 against the bias of the spring 112 can move the button out of engagement with a groove 120 formed in the locking shaft 114, allowing the shaft and the slider 106 to translate axially or proximally/distally relative to the button and the body. Releasing the button 110 can allow the button to return under the bias of the spring 112 into engagement with the groove 120 formed in the shaft 114 to limit axial translation of the shaft and the slider 106 relative to the button and the body 102.

The instrument 100 can include an actuation knob or other actuator 122. The actuation knob 122 can be mounted to the locking shaft 114. For example, the actuation knob 122 can define a central opening having interior threads that mate with exterior threads formed on the locking shaft 114. As described further below, the actuation knob 122 can be movable along the locking shaft 114 between a first position in which an implant disposed in the clamp 108 is locked from rotating relative to the instrument 100 about the axis A2 and a second position in which such an implant is retained to the instrument but allowed to rotate relative to the instrument about the axis A2.

Figure 4:
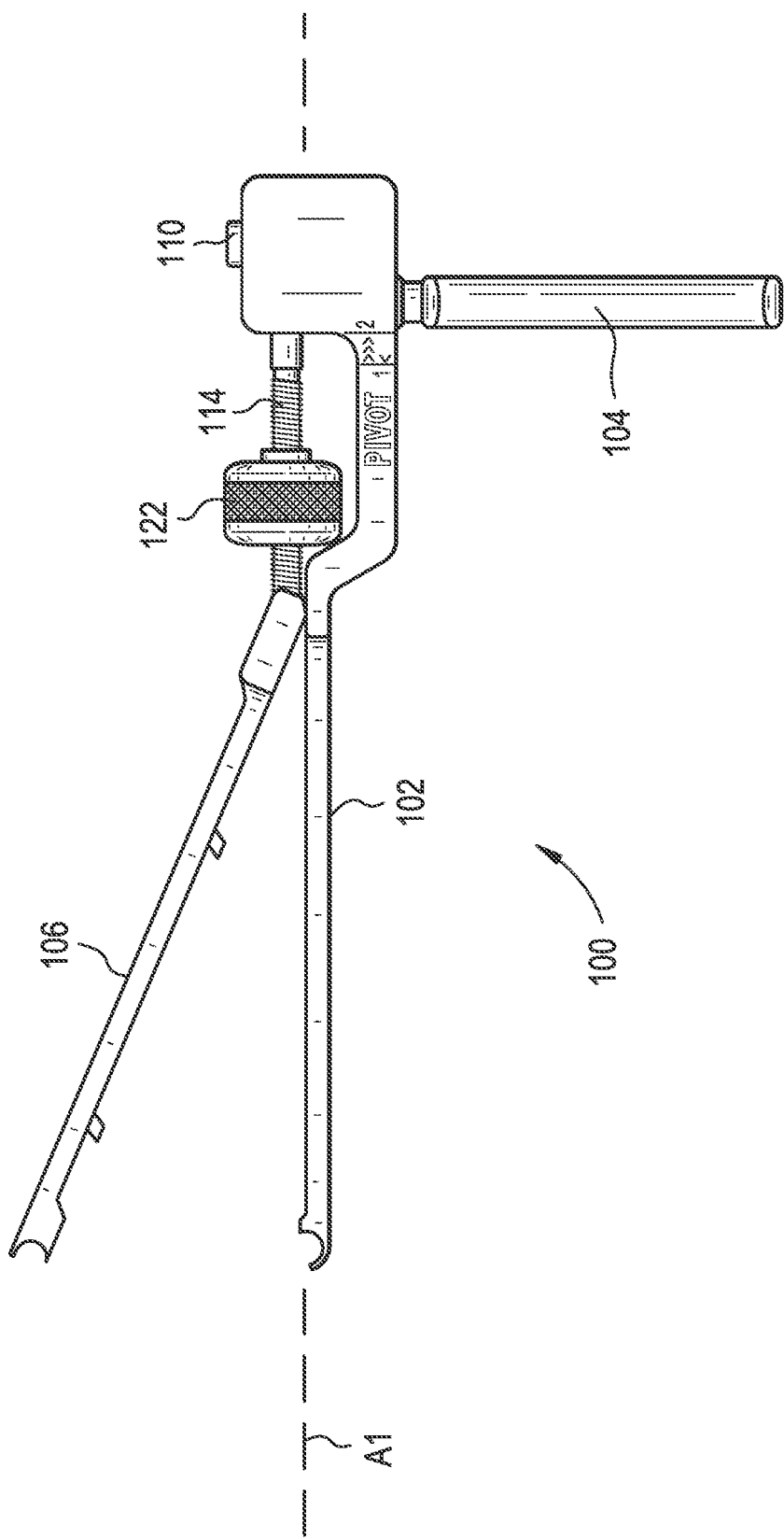
FIG. 4 illustrates a side view of the implant inserter of FIG. 1 in a disassembled state.

As shown in FIG. 4, the instrument 100 can be disassembled, e.g., for cleaning or sterilization. To disassemble the instrument 100, the actuation knob 122 can be rotated relative to the locking shaft 114 to move the knob along the locking shaft to a distal position. The button 110 can be depressed and the locking shaft 114 can be pulled distally out of the button and the body 102. The slider 106 can pivot about the first pin 116 to separate the slider from the body 102. The instrument 100 can thus be divided into a slider sub-assembly, e.g., including the slider 106, the locking shaft 114, and the actuation knob 122, and a body sub-assembly, e.g., including the body 102, the grip 104, the button 110, and the spring 112.

Figure 5:
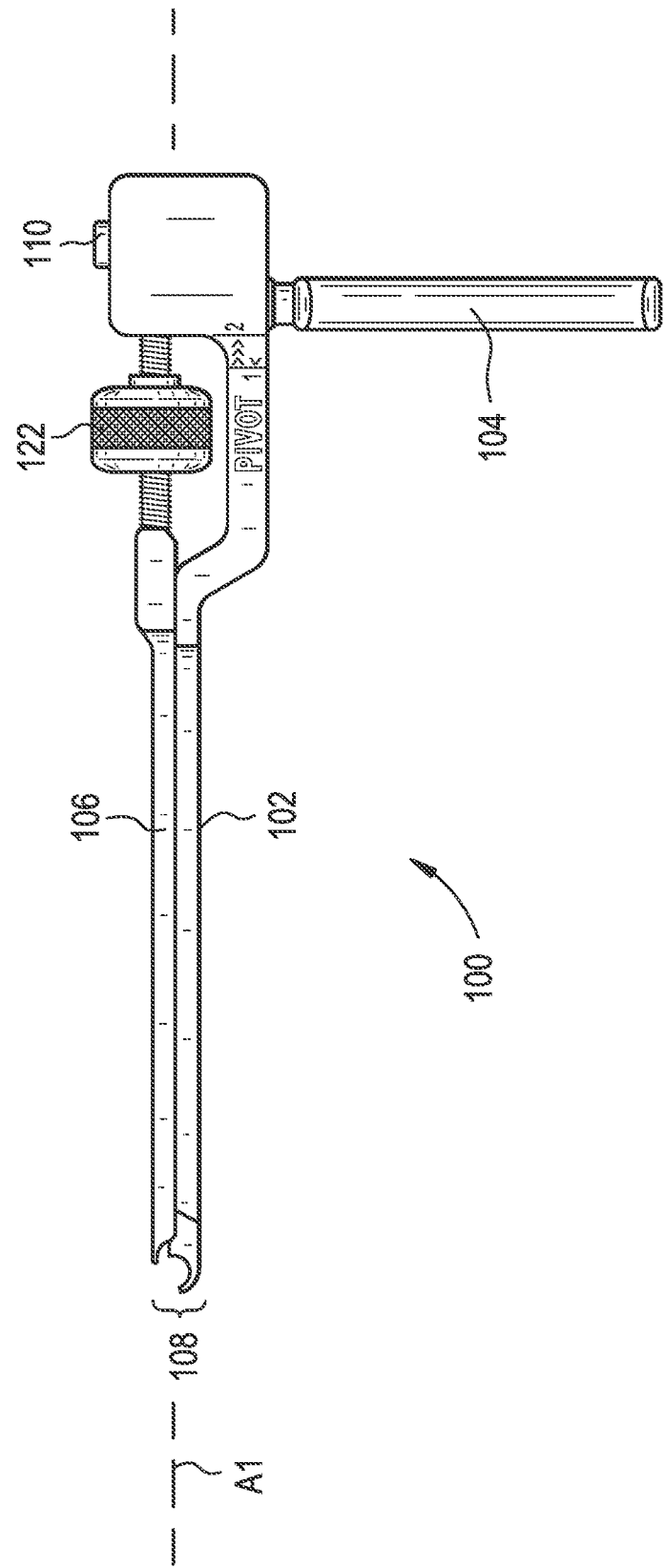
FIG. 5 illustrates a side view of the implant inserter of FIG. 1 in an implant receiving state.

As shown in FIG. 5, the instrument 100 can be positioned in an implant loading configuration in which it is prepared to receive an implant in the clamp 108. To position the instrument 100 in this configuration, the button 110 can be depressed to allow the slider sub-assembly to translate axially or proximally/distally relative to the body 102. The actuation knob 122 can then be pulled proximally to translate the slider 106 relative to the body 102 along the axis A1, thereby opening the implant clamp 108, i.e., positioning the distal end of the slider 106 far enough proximally to permit a portion of an implant to be received within a concave distal portion of the body 102. For example, the illustrated implant 5200 of FIG. 52 includes a first surface 5202 and a second surface 5204 separated from one another. A post 5206 extends between the two surfaces and can be configured to be received or surrounded by the implant clamp 108 to couple the implant to the instrument 100. As shown in FIG. 52, the post 5206 can include a plurality of flat surfaces arranged around its circumference and, in some embodiments, these surfaces can be aid in the selective prevention of rotation of the implant relative to the instrument by, for example, including one or more corresponding flat surfaces on distal ends of any of the body 102 or slider 106 such that a flat surface of the instrument can be abutted against a flat surface of the implant to prevent relative movement therebetween. In other embodiments, however, curved surfaces can be utilized in any of the implant, body, and slider.

Figure 6:
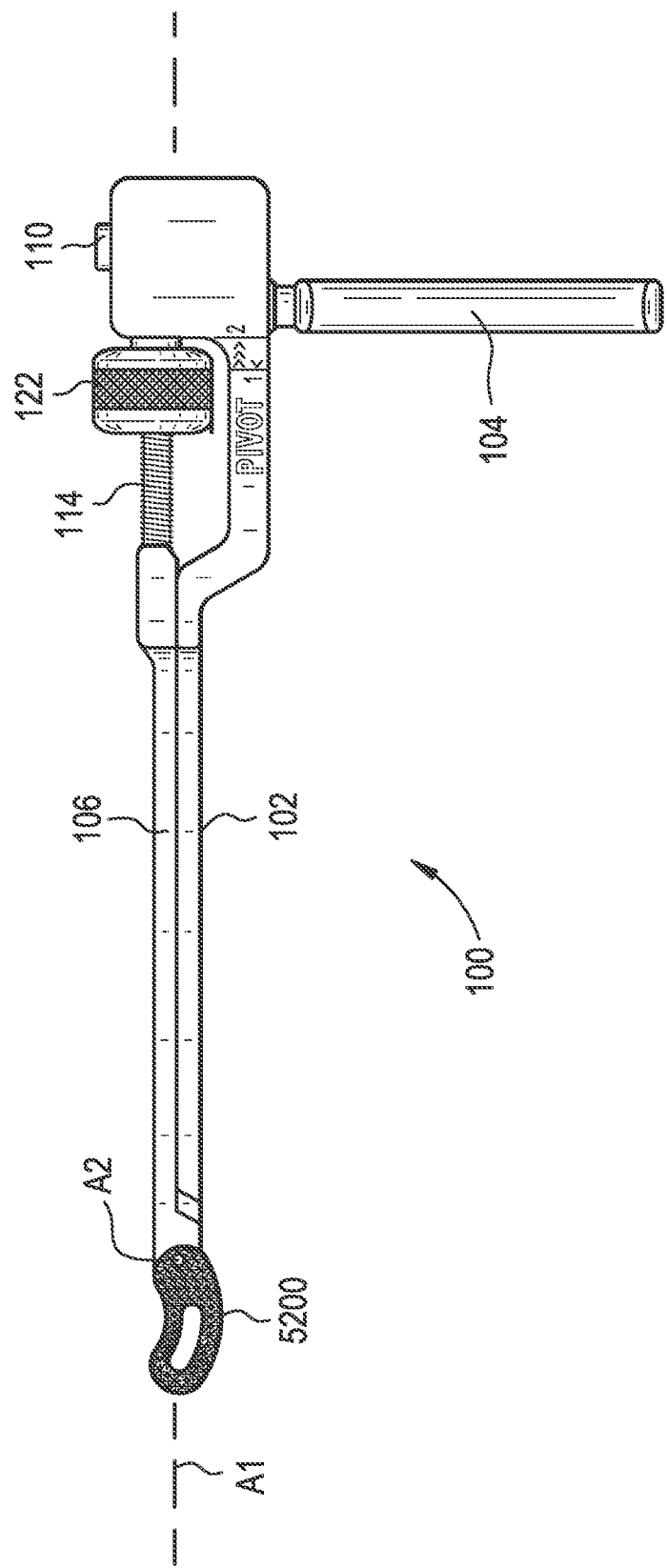
FIG. 6 illustrates a side view of the implant inserter of FIG. 1 with an implant retained thereto.

As shown in FIG. 6, once an implant (e.g., implant 5200) is positioned within the clamp 108, the slider 106 can be translated distally relative to the body 102 along the axis A1 to capture the implant within the clamp 108. In this configuration, the button 110 can be released such that the button engages the groove 120 formed on the locking shaft 114 to limit proximal movement of the slider 106 relative to the body 102 and to thereby retain the implant within the clamp 108.

Figure 7:
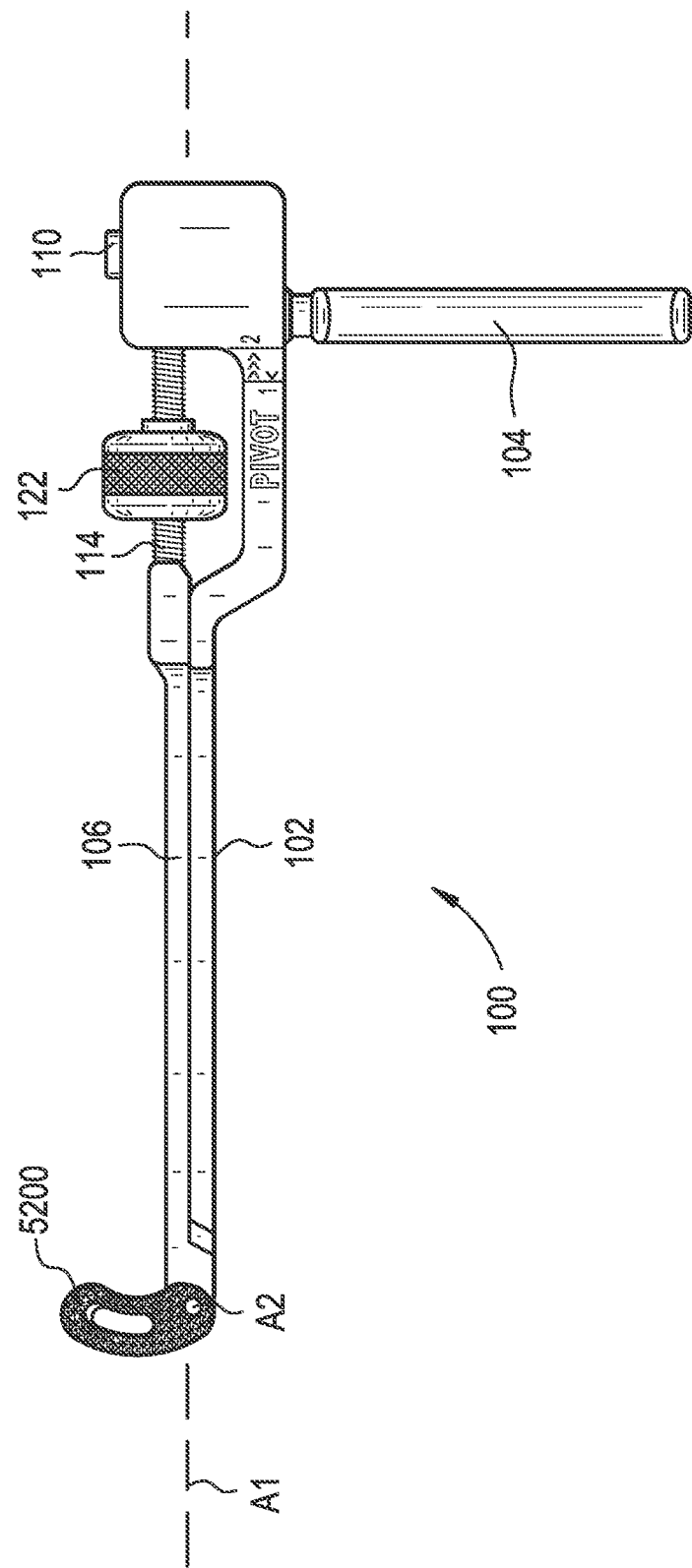
FIG. 7 illustrates a side view of the implant inserter of FIG. 1 with an implant articulated or rotated relative thereto.
Figure 8:
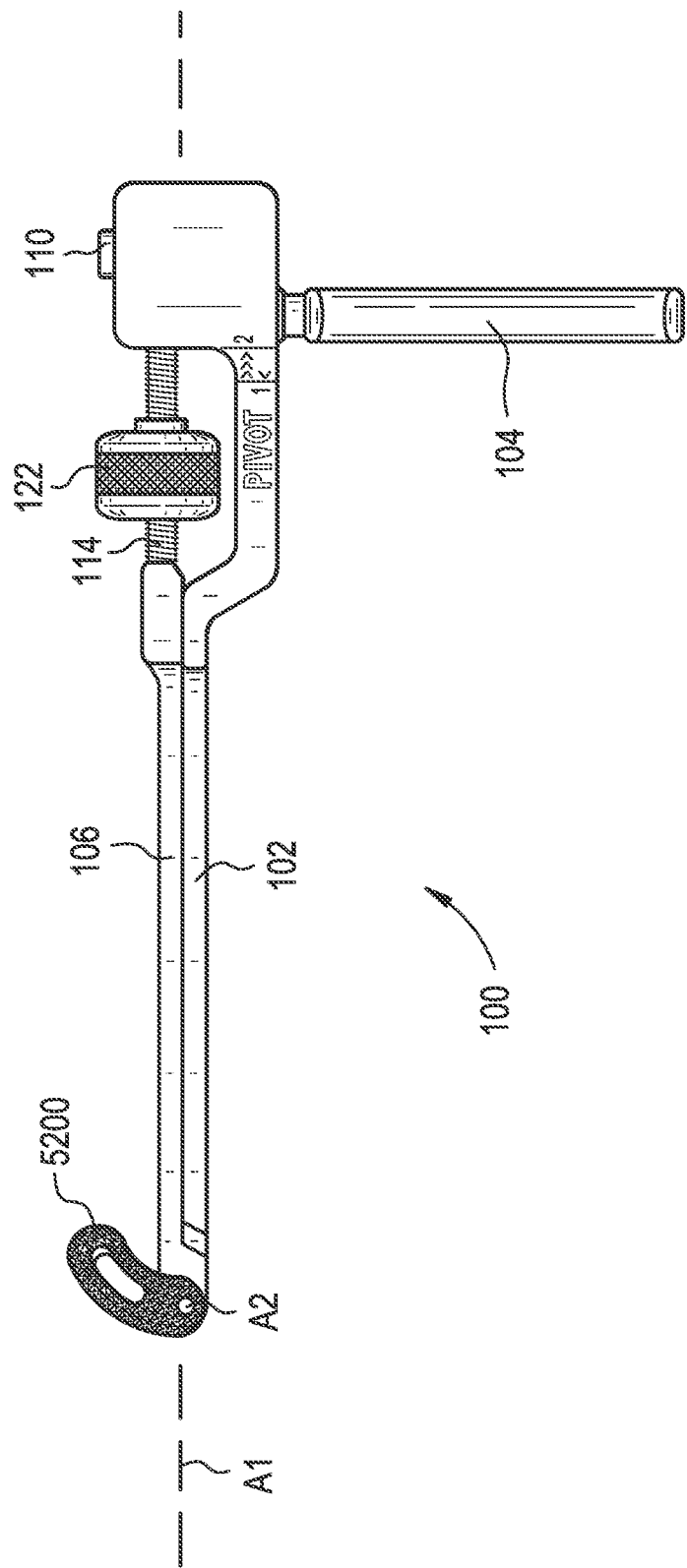
FIG. 8 illustrates an alternative view of the implant inserter of FIG. 1 with the implant articulated or rotated relative thereto.

As shown in FIGS. 6-7, the implant can be selectively permitted to rotate relative to the instrument 100 about the axis A2 when the implant is retained within the clamp 108. In particular, as shown in FIG. 6, the actuation knob 122 can be disposed in a first, proximal position in which an implant disposed in the clamp 108 is locked from rotating relative to the instrument 100 about the axis A2. To lock the implant from rotating relative to the instrument 100, the actuation knob 122 can be disposed in a proximal position on the locking shaft 114 in which the actuation knob abuts the body 102 to interfere with proximal translation of the slider 106 relative to the body. With the slider 106 urged distally and prevented from translating proximally, the implant can be firmly clamped to the instrument 100 such that the implant cannot rotate relative to the instrument about the axis A2. As shown in FIG. 7, the actuation knob 122 can be disposed in a second, distal position in which an implant disposed in the clamp 108 is retained to the instrument 100 but allowed to rotate relative to the instrument about the axis A2. The actuation knob 122 can be disposed in a distal position in which the actuation knob does not interfere with proximal translation of the slider 106 relative to the body 102. The groove 120 formed in the locking shaft 114 can be oversized in the proximal-distal direction relative to the engagement features of the button 110, such that some proximal movement of the slider 106 relative to the body 102 is permitted to allow articulation of the implant. The relative geometries of the button 110 and the groove 120, however, can be such that proximal translation of the slider 106 relative to the body 102 is not permitted to a degree that would allow the implant to separate from the instrument 100. As shown in FIG. 8, the instrument 100 can be configured such that a high degree of rotation of the implant about the axis A2 is permitted.

Figure 9:
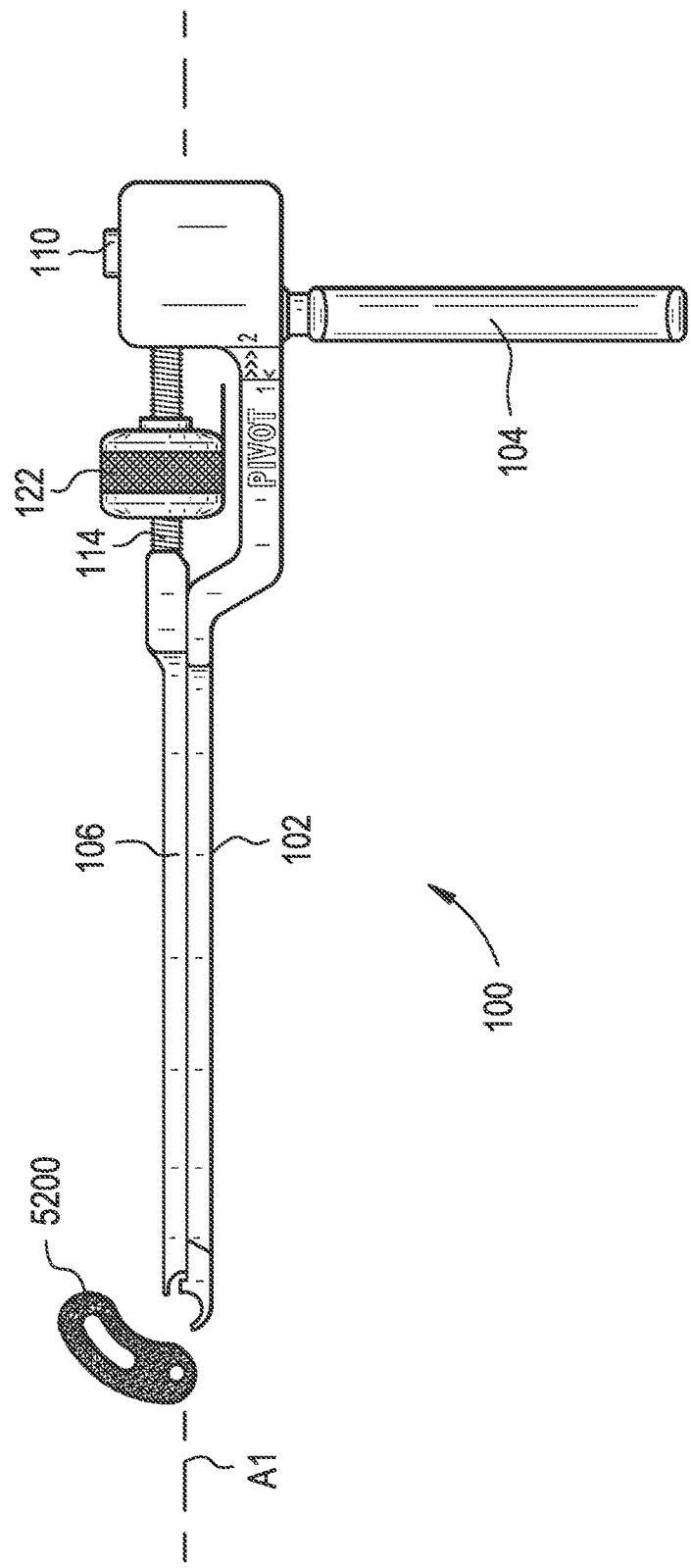
FIG. 9 illustrates a side view of the implant inserter of FIG. 1 releasing an implant.

As shown in FIG. 9, the instrument 100 can be disconnected from the implant, e.g., once the implant is placed as desired within the patient. The instrument 100 can be separated from the implant by pressing the button 110 and pulling the actuation knob 122 proximally to translate the slider 106 proximally relative to the body 102 and thereby open the clamp 108, similar to the configuration shown in FIG. 5 for loading the implant prior to insertion into a patient.

FIGS. 10-51 illustrate detailed views of the various components of the instrument 100. FIG. 52 illustrates an exemplary implant that can be used with the instrument 100.

Figure 10:
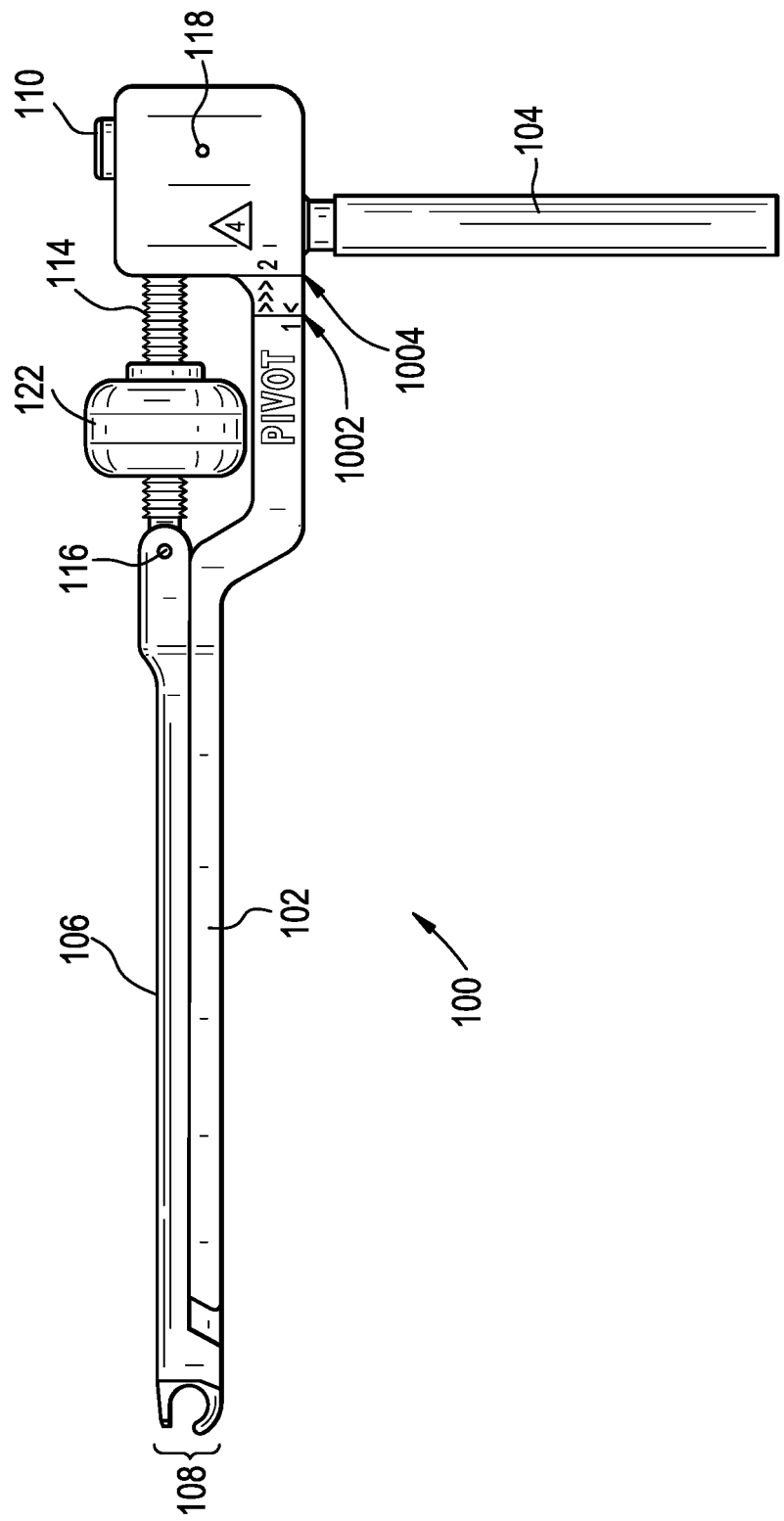
FIG. 10 illustrates an alternative side view of the implant inserter of FIG. 1.
Figure 12:
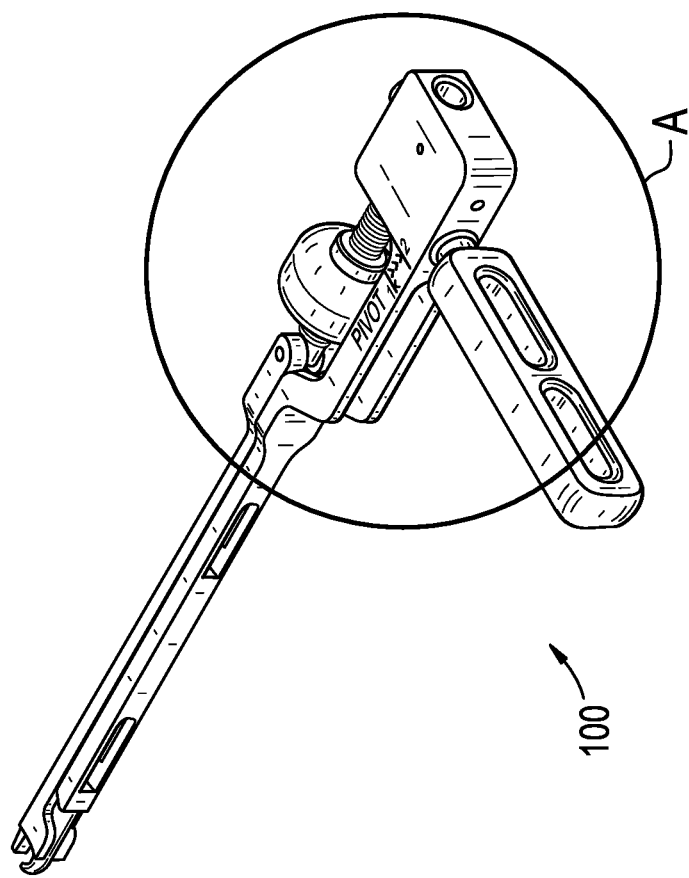
FIG. 12 illustrates an alternative perspective view of the implant inserter of FIG. 1.
Figure 11:
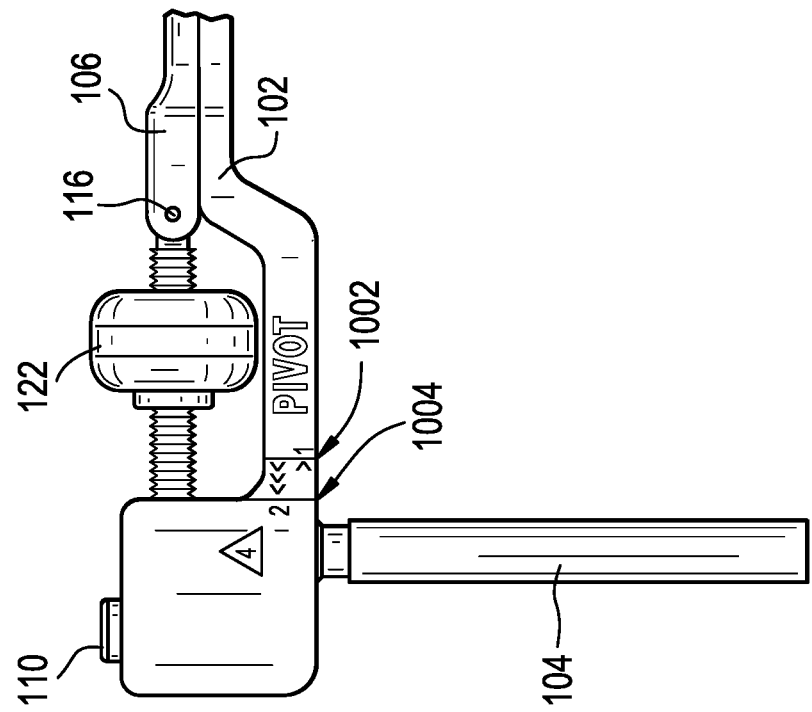
FIG. 11 illustrates a detail view of a portion of the implant inserter circled A in FIG. 12.
Figure 13:
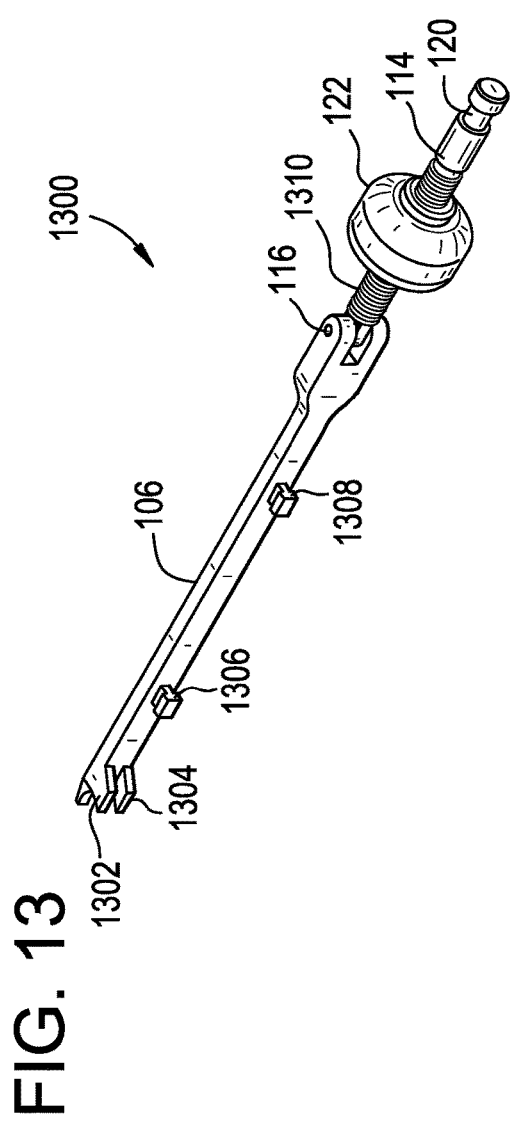
FIG. 13 illustrates a perspective view of the slider, locking shaft, and actuation knob of the implant inserter of FIG. 1.
Figure 16:
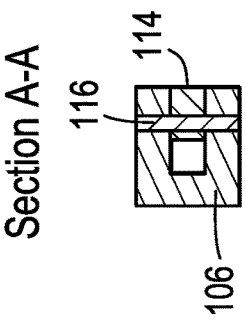
FIG. 16 is a cross-sectional view of the coupling between the slider and the locking shaft taken along the line A-A shown in FIG. 15.
Figure 14:
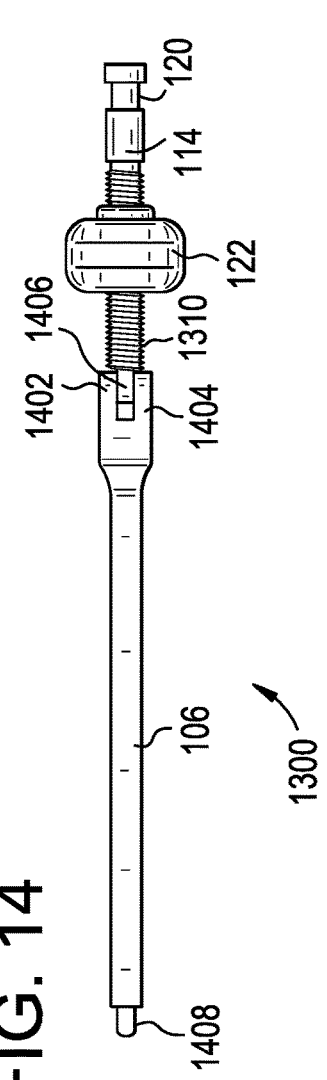
FIG. 14 is a top view of the components of FIG. 13.
Figure 15:
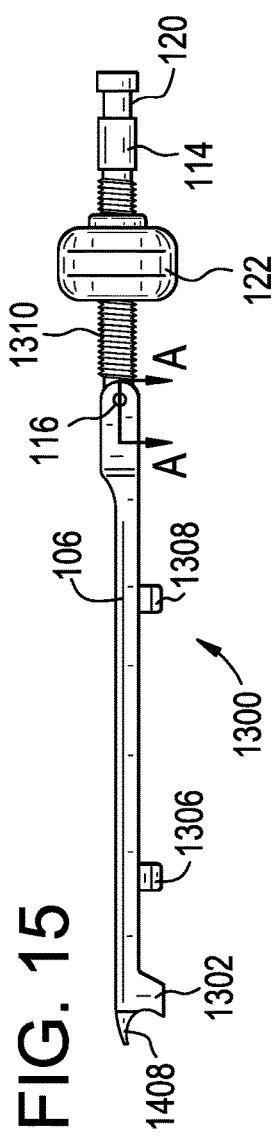
FIG. 15 is a side view of the components of FIG. 13.
Figure 25:
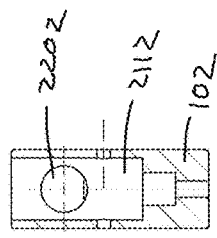
FIG. 25 is a cross-sectional view of the body of the implant inserter of FIG. 1 taken along the line B-B shown in FIG. 22.

FIGS. 10-12, for example, show detailed side views of the instrument 100, including the proximal portion of the boxy 102. In these figures, the actuation knob 122 is shown positioned distally beyond the pivot positioning marker 1002. When the knob is in such a position and the button 110 is depressed, the slider 106 can be advanced distally and rotated about pin 116 away from the body 102, as shown in FIG. 4. Conversely, when full locking of the implant within the clamp 108 is desired, the actuation knob 122 can be positioned proximally such that it abuts against the body 102 and is in line with the lock positioning marker 1004.

FIGS. 13-16 illustrate the above-mentioned slider sub-assembly 1300, which can include the slider 106, locking shaft 114, pin 116, and actuation knob 122. The slider 106 can be coupled to the locking shaft 114 using a clevis joint, e.g., with a proximal end of the slider 106 forming a U-shaped clevis with opposed arms 1402, 1404 that receive a tang 1406 formed at a distal end of the locking shaft 114. The components can be held together by the pin 116 such that they can pivot about the pin's longitudinal axis but cannot rotate relative to one another about a central longitudinal axis of the slider or locking shaft.

The slider 106 can include a distal end 1408 configured to form part of the clamp 108, as well as distal guide surfaces 1302, 1304 configured to ride along the sides of an elongate distal portion of the body 102 to maintain alignment of the slider and the body. The slider 106 can also include one or more protrusions 1306, 1308 configured to be received within recesses formed in the body 102 to maintain alignment of the slider and the body and prevent inadvertent pivoting of the components away from one another. The protrusions 1306, 1308 can have any of a variety of shapes but in some embodiments can have a T-track or other shape that can be received through a larger opening and subsequently translated into a smaller opening to prevent separation but allow for translation between the slider and the body.

As noted above, the locking shaft 114 can include the groove 120 formed in a proximal portion thereof, as well as the aforementioned distal end 1406 configured to couple to the proximal end of the slider 106. A portion of the locking shaft 114 between the groove 120 and the distal end 1406 can have external threads 1310 formed thereon. The external threads 1310 can be configured to mate with threads formed on an internal surface of a central opening formed in the actuation knob 122 to allow rotation of the knob to control translation of the slider 106 relative to the body 102, as described herein.

FIGS. 17-20 illustrate the above-mentioned body subassembly 1700, which can include the body 102, grip or handle 104, button or other actuator 110, and spring or other biasing element 112. The grip or handle 104 can be coupled to the body 102 in a variety of manners, including via a threaded connection, a press fit interference connection, welding, adhesive, etc. The handle 104 can extend from the body 102 such that a longitudinal axis A3 of the handle is perpendicular to the central longitudinal axis A1 of the instrument. Alternatively, the handle 104 can be arranged to extend from at a different angle such that the axes A3 and A1 cross one another at an oblique angle.

The push button or other actuator 110 can be disposed in a first bore (see FIG. 21) formed in the body 102 along with the spring or other biasing element 112. The pin 118 can retain the button 110 within the first bore while allowing movement through a desired range of motion. As explained in more detail below, the button 110 can include an aperture formed therein that can at least partially align with a second bore formed in the body 102 to receive the locking shaft 114.

FIGS. 21-26 illustrate the body 102 in greater detail. A distal portion of the body 2106 can have a shape to receive a portion of an implant, such as the implant 5200 of FIG. 52. The portion 2106 can, for example, have a curved semi-circular shape that can receive a portion of an implant and, in connection with a correctly-positioned distal portion of the slider 106, retain the implant between the slider and the body.

Figure 24:
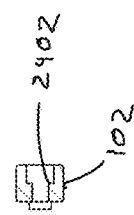
FIG. 24 is a cross-sectional view of the body of the implant inserter of FIG. 1 taken along the line D-D shown in FIG. 21.
Figure 26:
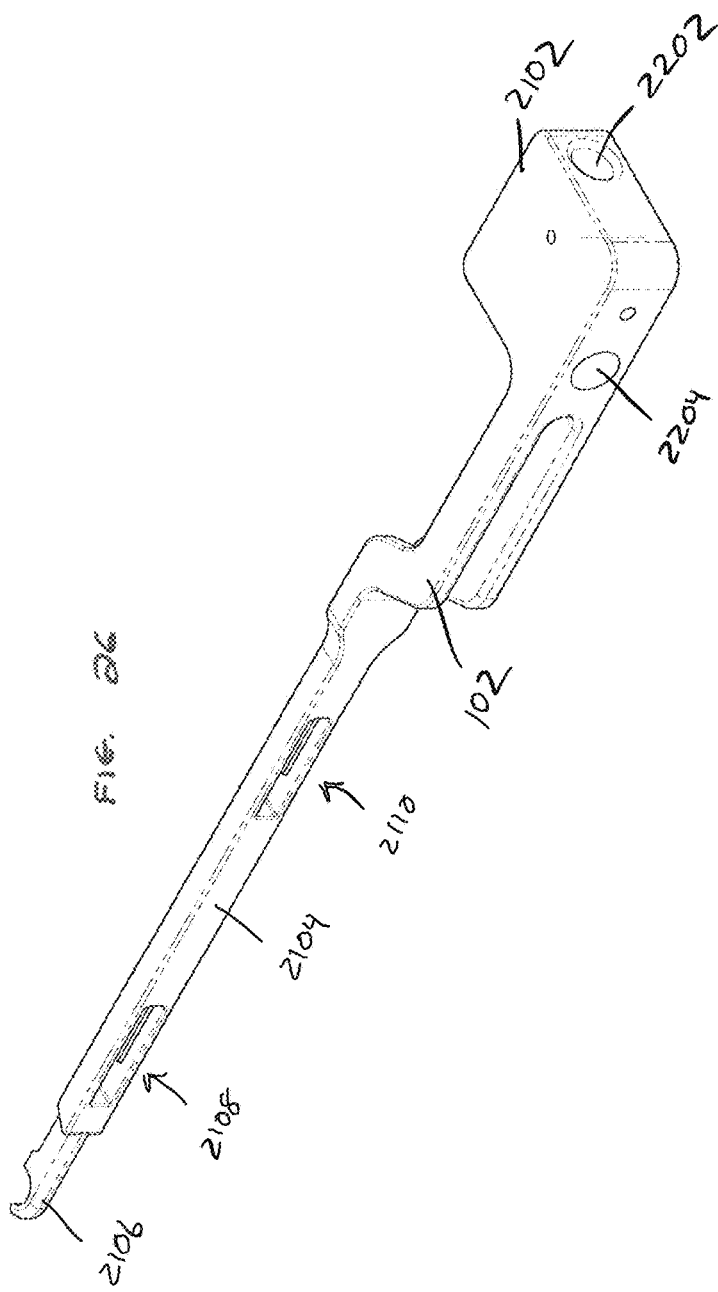
FIG. 26 is a perspective view of the body of the implant inserter of FIG. 1.

The distal portion 2106 can be disposed at an end of an elongate distal portion 2104 of the body 102 that extends from a proximal portion 2102. Spaced along the elongate distal portion 2104 can be one or more apertures 2108, 2110 configured to receive the one or more protrusions 1306, 1308 formed on the slider 106. Each aperture, e.g., aperture 2108, can include a larger distal opening 2108a configured to receive the protrusion 1306 when the slider is pivoted into parallel alignment with the body 102, as well as a narrower proximal opening 2108b configured to receive only a narrower portion of the protrusion 1306 (e.g., when the protrusion has a T shape, etc.) to permit translation of the slider relative to the body while preventing the slider from pivoting away from the body. A cross-sectional view of a shoulder 2402 that can be used to achieve this effect is shown in FIG. 24.

Turning to the proximal portion 2102 of the body 102, FIGS. 21-26 illustrate the first bore 2112 that is configured to receive the push button 110 and spring 112. Also shown is the second bore 2202 that is configured to receive the locking shaft 114. The first and second bores 2112, 2202 cross one another such that the locking shaft 114 can extend through an aperture formed in the button 110. Also shown in the figures is a third bore 2204 formed in the body 102 and configured to receive an end of the handle or grip 104.

FIGS. 27-36 illustrate the slider 106 in greater detail. Visible features include the T-shaped protrusions 1306, 1308, the proximal clevis U-shaped arms 1402, 1404, the distal guides 1302, 1304, and the distal end 1408 described above. Of note in these figures is the fact that the guides 1302, 1304 can be configured to contact the portion of the implant disposed between distal ends of the slider 106 and the body 102 in the implant clamp 108. Accordingly, the guides 1302, 1304 can provide additional surface area for securely gripping the implant and preventing any relative movement, e.g., rotation, of the implant relative to the instrument 100 when in the locked configuration shown in FIG. 6.

FIG. 37 illustrates the grip or handle 104 in isolation, including a protrusion 3702 formed at one end thereof that can be configured to extend into the bore 2204 and be secured using any of a variety of techniques known in the art. Also shown is the central longitudinal axis A3 of the handle 104 that can be configured to extend from the instrument such that it is perpendicular to the central longitudinal axis of the instrument A1, as shown in FIG. 1. In other embodiments, however, the handle can be configured to extend at a different angle from the body 102 such that the axes A1, A3 are oblique to one another.

FIGS. 38-40 illustrate the locking shaft 114 in isolation. Visible in the figure are the above-described distal tang 1406, the proximal groove 120, and the intermediate portion having external threads 1310 formed thereon. As noted above, the groove 120 can have an oversize length L extending axially along the shaft to allow some degree of proximal/distal translation of the shaft relative to the body even when the button 110 is positioned so as to retain the shaft to the body 102.

FIGS. 41-43 illustrate the actuation knob 122 in isolation. As noted above, the actuation knob 122 can include a central opening 4102 formed therein and an internal surface of the opening can include threads 4104 formed thereon. The threads 4104 can be configured to mate with the external threads 1310 formed on the locking shaft 114, as described herein. An outer surface of the actuation knob 122 can include surface features to facilitate a user gripping and rotating the knob, such as surface knurling 4302 or other similar features.

FIGS. 44-48 illustrate various views of the push button or other actuator 110. The button 110 can include an aperture formed therethrough that can be configured to receive the locking shaft 114. The aperture can have a first circular diameter $D_1$ extending through an entire thickness of the button 110, as well as partial-thickness cut-outs extending from each end of the aperture having a larger elliptical shape with major diameter $D_2$ and a minor diameter of $D_1$. This can create an aperture or through-hole having a ridge 4404 extending into the aperture or through-hole 4402. The ridge 4404 can have a size configured to interface with the groove 120 formed in the locking shaft 114 such that, when the ridge 4404 is disposed within the groove 120, the locking shaft can only be moved proximally or distally until the ridge abuts one of a proximal or distal sidewall of the groove 120. Because the ridge is formed on the bottom of the aperture 4402, the biasing element 112 can urge the button 110 upward and urge the ridge 4404 into the groove 120 when a user releases the button 110. Conversely, when a user depresses the button 110 and disposes the locking shaft 114 in the upper portion of the aperture 4402 above the ridge 4404, the locking shaft 114 can be withdrawn from the aperture 4402.

The upward or downward travel of the button 110 can be limited by the pin 118 that can be disposed within a second aperture 4502 formed through the button 110. As shown, the second aperture 4502 is perpendicularly oriented relative to the aperture 4402, but in other embodiments a different configuration can be utilized. The second aperture 4502 can have an elliptical cross section with a major diameter that can define the range of movement for the button 110 (because the pin 118 can be stationary relative to the body 102 when disposed through apertures formed therein that substantially match the diameter of the pin). This dimension can be configured to substantially match, for example, a depth of the groove 120 and height of the ridge 4404 in some embodiments.

FIGS. 49-51 illustrate the spring 112 and pins 116, 118 in isolation. These components are known in the art, e.g., conventional coil springs and cylindrical pins. In some embodiments, any of a variety of alternatives known in the art can be substituted for the elements shown in these figures.

In use, the instrument 100 can be configured as shown in FIG. 4 and can be cleaned and/or sterilized to prepare the instrument for surgery. A fusion cage or other implant can be loaded onto the instrument 100 and locked in the position shown in FIG. 6. The instrument 100 can then be used to deliver the implant to a target site within a patient, for example by passing the implant into a spinal disc space through a minimally-invasive working channel and/or using a TLIF approach. Once the implant is disposed within the disc space, or at any other time desired by the user, the instrument 100 can be configured as shown in FIG. 7 and the implant can be rotated relative to the instrument about the axis A2, e.g., to either of the positions shown in FIGS. 7 and 8. The instrument 100 can then be disconnected from the implant as shown in FIG. 9, and the surgical procedure can be completed using known techniques.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The instruments disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can be rigid or flexible. Device sizes can also vary greatly, depending on the intended use and surgical site anatomy. Furthermore, particular components can be formed from a different material than other components. One or more components or portions of the instruments can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The instruments and methods disclosed herein can be used in minimally-invasive surgery and/or open surgery. While the instruments and methods disclosed herein are generally described in the context of spinal surgery on a human patient, it will be appreciated that the methods and instruments disclosed herein can be used in any type of surgery on a human or animal subject, in non-surgical applications, on non-living objects, and so forth.

The devices disclosed herein can be designed to be disposed after a single use, or they can be designed for multiple uses. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

All papers and publications cited herein are hereby incorporated by reference in their entirety. Although specific embodiments are described above, it should be understood that numerous changes may be made within the spirit and scope of the concepts described. Accordingly, the disclosure is not to be limited by what has been particularly shown and described, except as indicated by the appended claims.

The invention claimed is:

1. A surgical instrument, comprising:
a body having an elongate distal portion and a handle extending from a proximal portion of the body;
a slider coupled to the body and extending parallel to the elongate distal portion of the body, wherein distal ends of the slider and the body collectively define an implant clamp;
a locking shaft coupled to a proximal end of the slider and received within a first bore formed in the proximal portion of the body;
a first actuator disposed within a second bore formed in the proximal portion of the body, the first actuator being configured to selectively limit proximal and distal translation of the slider relative to the body;
a second actuator disposed about the locking shaft that is also configured to limit proximal and distal translation of the slider relative to the body;
wherein the first actuator and the second actuator can be configured to selectively retain an implant within the implant clamp and selectively allow rotation of the implant relative to the instrument,
wherein the second actuator is a knob including a central opening having interior threads that mate with exterior threads formed on the locking shaft.

2. The instrument of claim 1, wherein the body has a central longitudinal axis extending between the proximal and distal portions, and the clamp is configured to selectively allow rotation of the implant about a rotation axis that is perpendicular to the central longitudinal axis.

3. The instrument of claim 2, wherein the handle extends from the body such that a central longitudinal axis of the handle is transverse to the central longitudinal axis of the instrument;
wherein the rotation axis is perpendicular to a plane defined by the central longitudinal axis of the instrument and the central longitudinal axis of the handle.

4. The instrument of claim 1,
wherein a proximal end of the locking shaft includes a groove formed therein and a central portion of the locking shaft includes the exterior threads formed thereon.

5. The instrument of claim 4, wherein the first actuator is configured to move between a first position to couple the locking shaft to the body and a second position to release the locking shaft from the body.

6. The instrument of claim 5, wherein the first actuator is biased toward the first position.

7. The instrument of claim 5, wherein the first actuator is configured to couple the locking shaft to the body by disposing a portion thereof within the groove formed in the locking shaft.

8. The instrument of claim 7, wherein the groove in the locking shaft is sized such that some degree of proximal and distal translation of the locking shaft relative to the first actuator and the body is possible when the actuator is in the first position.

9. The instrument of claim 1, wherein the clamp is configured to selectively allow rotation of the implant about a rotation axis that is perpendicular to a central longitudinal axis of the instrument extending between a proximal end of the body and the distal end of the body.

10. The instrument of claim 9, wherein the handle extends from the proximal portion of the body such that a central longitudinal axis of the handle is transverse to the central longitudinal axis of the instrument;
wherein the rotation axis is perpendicular to a plane defined by the central longitudinal axis of the instrument and the central longitudinal axis of the handle.

11. The instrument of claim 1, wherein the knob is movable between a first position in which the clamp is configured to retain the implant to the instrument without allowing the implant to rotate relative to the instrument and a second position in which the clamp is configured to retain the implant to the instrument while allowing the implant to rotate relative to the instrument.

* * * * *